United States Patent
Yano et al.

(10) Patent No.: US 6,828,074 B2
(45) Date of Patent: Dec. 7, 2004

(54) BINDER RESIN CONTAINING POLYHYDROXYALKANOATE, TONER CONTAINING THE BINDER RESIN, AND IMAGE-FORMING METHOD AND IMAGE-FORMING APPARATUS WHICH MAKE USE OF THE TONER

(75) Inventors: Tetsuya Yano, Kanagawa (JP); Etsuko Sugawa, Kanagawa (JP); Takeshi Imamura, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 128 days.

(21) Appl. No.: 10/133,578

(22) Filed: Apr. 29, 2002

(65) Prior Publication Data

US 2003/0073019 A1 Apr. 17, 2003

(30) Foreign Application Priority Data

Apr. 27, 2001 (JP) .......................................... 2001-133549

(51) Int. Cl.[7] .............................................. G03G 9/087
(52) U.S. Cl. .................................. 430/109.1; 430/109.2
(58) Field of Search ............................. 430/109.1, 109.2

(56) References Cited

U.S. PATENT DOCUMENTS

| 5,004,664 A | 4/1991 | Fuller et al. ............. 430/106.6 |
|---|---|---|
| 5,292,860 A | 3/1994 | Shiotani et al. ............. 528/361 |
| 5,667,927 A | 9/1997 | Kubota et al. ............... 430/109 |
| 5,760,144 A | 6/1998 | Ozeki et al. ................. 525/450 |
| 6,266,272 B1 | 7/2001 | Kirihata et al. ........ 365/185.08 |

FOREIGN PATENT DOCUMENTS

| JP | 5-93049 | 4/1993 |
|---|---|---|
| JP | 6-289644 | 10/1994 |
| JP | 7-82352 | 3/1995 |
| JP | 7-120975 | 5/1995 |
| JP | 7-265065 | 10/1995 |
| JP | 8-262796 | 10/1996 |
| JP | 8-289797 | 11/1996 |
| JP | 9-20857 | 1/1997 |
| JP | 9-87499 | 3/1997 |
| JP | 9-274335 | 10/1997 |
| JP | 2001-46094 | 2/2001 |
| JP | 2001-57085 | 2/2001 |
| WO | WO 00/43523 | 7/2000 |

OTHER PUBLICATIONS

Fukui, et al.; "Cloning and Analysis of . . . *caviae*"; J. Bact. 179, 15, 4821–4830 (1997).

*Primary Examiner*—Mark A. Chapman
(74) *Attorney, Agent, or Firm*—Fitzpatrick, Cella, Harper and Scinto

(57) ABSTRACT

A polyhydroxyalkanoate (PHA) comprised of two kinds of units, a 3-hydroxybutyrate (3HB) unit and a 3-hydroxyhexanoate (3HHx) unit is used as a binder resin. This provides a binder resin which is biodegradable and can more highly contribute to the conservation of natural environment.

10 Claims, 7 Drawing Sheets

BINDER RESIN CONTAINING POLYHYDROXYALKANOATE, TONER CONTAINING THE BINDER RESIN, AND IMAGE-FORMING METHOD AND IMAGE-FORMING APPARATUS WHICH MAKE USE OF THE TONER

BACKGROUND OF THE INVENTION

1. Field of the Invention

This invention relates to a binder resin usable in toners for developing electrostatic latent images, a toner for developing electrostatic latent images, an image-forming method making use of the toner and an image-forming apparatus making use of the toner. More particularly, it relates to a binder resin, a toner for developing electrostatic latent images, an image-forming method and an image-forming apparatus which are used in electrophotography, electrostatic recording and electrostatic printing performed in copying machines, printers, facsimile machines and so forth, in which a toner image is previously formed on an electrostatic-latent-image-bearing member (hereinafter simply "image-bearing member") and is thereafter transferred onto a transfer medium to form an image. Still more particularly, it relates to a binder resin which has a biodegradability and at the same time contributes to superior fixing performance (low-temperature fixing performance, fixing temperature characteristics and anti-offset properties) and blocking resistance, and which has hydrolyzability and biodegradability and can readily be deinked, where existing deinking systems can be utilized as they are, also enabling waste disposal with ease; a toner for developing electrostatic latent images which contains such a binder resin; and an image-forming method and an image-forming apparatus which make use of the toner.

2. Related Background Art

A number of methods are conventionally known as methods for electrophotography. In general, copies are obtained by forming an electrostatic latent image on an image-bearing member (photosensitive member) by utilizing a photoconductive material and by various means, subsequently developing the latent image by the use of a toner to form a visible image (toner image), transferring the toner image to a transfer medium as occasion calls, and then fixing the toner image to the transfer medium by heating and/or pressing. As methods by which the electrostatic latent image is formed into a visible image, cascade development, magnetic brush development, pressure development and so forth are known in the art. Another method is also known in which, using a magnetic toner and a rotary developing sleeve provided with magnetic poles at the core, the magnetic toner is caused to fly from the developing sleeve surface to the photosensitive member surface by the aid of an electric field.

As development methods used when electrostatic latent images are developed, available are a two-component development method making use of a two-component type developer comprised of a toner and a carrier and a one-component development method making use of no carrier and comprised only of a toner.

Now, fine colored particles commonly called a toner are constituted of a binder resin and a colorant as essential components and besides optionally a magnetic material and so forth. Here, the binder resin occupies the greater part of the toner, and hence the physical properties of such a binder resin influence toner's physical properties greatly. For example, the binder resin is required to have delicate hardness and thermal melt properties, and a toner obtained by pulverizing a binder resin having a colorant and so forth dispersed therein followed by classification must show good fluidity without producing any fine powder against a mechanical impact caused by agitation in a developing assembly and also without causing agglomeration of the toner itself. Also, at the time of fixing, the toner must immediately melt at a low temperature and, when melts, the molten toner must show agglomeration properties. Namely, the controlling of binder resin's physical properties enables control of toner's physical properties.

As the binder resin, conventionally used are a styrene-acrylate copolymer, polyester resin, epoxy resin, olefinic resin and so forth. In particular, polyester resin is widely used at present as a resin for toners for heat-roll fixing, because, e.g., it has advantages such that, when melt, it makes toner additives such as carbon black disperse well and is well wettable to transfer paper.

In recent years, from the viewpoint of environmental conservation, it is also of worldwide consciousness how resources be recycled, how waste be curtailed, how the safety of waste be improved, and so forth. Such a subject is not exceptional also in the field of electrophotography. More specifically, with wide spread of copying machines and printers, the disposal of fixed toner on paper, waste toner after use, printed paper, copying paper and so forth is increasing year by year. Here, conventional toners are sparingly degradable because they are constituted of components all of which are stable artificial compounds, and may remain in all environment, e.g., in soil and in water over a long period of time. Hence, there is a possibility that they may come to be a source of environmental pollution when toners having been used are, e.g., buried in soil for their disposal. Also, in order to recycle resources, it is one of important subjects to regenerate plain paper for its reuse. However, conventional binder resins composed chiefly of styrene resins, it is difficult to remove them from paper surface (deinking) by alkali hydrolysis. This has come to be one of difficulties in the recycling of plain paper. The safety of waste is also an important subject from the standpoints of the conservation of global environment and the influence on human bodies.

Under such circumstances, development is being made on resins which are harmless to human bodies and degradable by the action of microorganisms, i.e., biodegradable resins. For example, it has been reported that many microorganisms are capable of producing a biodegradable resin having a polyester structure (polyhydroxyalkanoate; hereinafter abbreviated "PHA") and accumulating it in the bacterial body ("Handbook of Biodegradable Plastics", Biodegradable-Plastic Institute, K.K. NTS, pp.178–197, 1995). It is known that such a PHA can have various compositions and structures depending on the type of microorganisms used for its production, the composition of culture medium, the conditions for culturing and so forth. Researches on how to control the composition and structure of the PHA to be produced have hitherto chiefly been made from the viewpoint of the improvement in its physical properties. With regard to the application of such biodegradable resins, they have already given reasonable actual results especially in the field of materials for medical use. In the field of agriculture, too, the biodegradable resins have been put into practical use in multifiles, gardening material, sustained-release agricultural chemicals, fertilizers and so forth. In the field of leisure industry, too, the biodegradable resins are used in fishing lines, fishing articles, golf goods and so forth. Besides, as packaging materials for daily necessities, they have been put into practical use in containers or the like of living articles. However, considering their wide application as plastics, under the existing conditions they can not still be said to be satisfactory in respect of physical properties. For example, in order to make the PHA utilizable in much wider ranges, it is important to study the improvement of physical properties more widely. For that end, it is essential to make development and research on PHAs containing monomer units of various structures.

In the field of electrophotography, too, methods in which biodegradable resins are used in binder resins are proposed as methods by which toners which are disposable without causing environmental pollution are realized. For example, Japanese Patent Application Laid-Open No. 6-289644 discloses an electrophotographic toner particularly used for heat-roll fixing, which is characterized in that at least a binder resin contains a vegetable wax and a biodegradable resin (as exemplified by polyesters produced by microorganisms and natural polymeric materials derived from vegetables or animals), and the vegetable wax is added to the binder resin in an amount of from 5 to 50% by weight. Japanese Patent Application Laid-Open No. 8-262796 also discloses an electrophotographic toner containing a binder resin and a colorant, which is an electrophotographic toner characterized in that the binder resin comprises a biodegradable resin (as exemplified by aliphatic polyester resins) and the colorant comprises a water-insoluble coloring matter. Also, U.S. Pat. No. 5,004,664 discloses a toner having as its composition polyhydroxybutyric acid, polyhydroxyvaleric acid, or a copolymer or blend of these.

In these techniques, when buried for disposal, toners can certainly be degraded in soil because the binder resins are biodegradable. However, there have been problems on fundamental function as binder resins, such that the toner has a low running performance and also is unstably chargeable because of its high moisture absorption. For example, the PHA is a hard and brittle material having properties of a melting point of 180° C., a crystallinity of 50 to 70%, a Young's modulus of 3.5 GPa and a breaking extension of 5%, and is insufficient in practical use for its use as the binder resin of toner.

A toner composed chiefly of a polylactic acid type aliphatic polyester is also proposed as having a biodegradability and also being efficiently degradable in alkali hydrolysis and hence being useful for the recycling of paper. For example, Japanese Patent Application Laid-Open No. 7-120975 discloses a method of making a lactic-acid homopolymer into a toner, giving as its typical example a polylactic acid obtained by ring-opening polymerization. In the ring-opening polymerization, a method is employed in which the lactic acid is first made into an oligomer by dehydration reaction, which oligomer is then subjected to depolymerization to lead it to a cyclic dimer lactide and is further subjected to ring-opening polymerization.

Since such complicate steps are followed, the resultant polylactic acid comes very highly expensive for its use as a toner resin (a resin for toners). Also, since the ring-opening polymerization is cationic ring-opening polymerization, it is necessary, e.g., to make anhydrous the solvent used and to remove any ionic species which may serve as a polymerization terminator, resulting in a poor production efficiency. Moreover, the monomer species that can be used when the polyester is produced is limited to a cyclic ester, and hence it is not easy to control physical properties required as toner resins. It is also difficult to effect copolymerization with various monomers in order to control the balance between degradability and physical properties. In this regard, it is sought to provide a degradable polyester that can control its physical properties inexpensively and with ease. Also, when the polylactic acid is made into a toner as it is, there are problems also on the storage stability and anti-offset properties of the toner. Thus, such a toner has not yet been put into practical use.

Japanese Patent Application Laid-Open No. 9-274335 also discloses a toner for developing electrostatic latent images which is characterized by containing a polyester resin and a colorant; the former being obtained by dehydration polycondensation of a composition containing lactic acid and a tri- or more functional oxycarboxylic acid. However, the polyester resin is formed through dehydration polycondensation reaction of an alcohol group of the lactic acid with a carboxylic group in the oxycarboxylic acid. Hence, it is considered that the resultant resin tends to have a large molecular weight, and therefore has a low biodegradability. Also, like the one disclosed in Japanese Patent Application Laid-Open No. 7-120975, there are problems on the storage stability and anti-offset properties of the toner.

Polycaprolactone, which is a homopolymer of a typical hydroxycarboxylic acid, also has a low melting point and a low glass transition point and has good compatibility with various resins. It, however, has a melting point of as low as 60° C., and is not suitable as a binder resin when used alone. Also, the polylactic acid has a high glass transition point (60° C.), and one having crystallizability is a thermoplastic high polymer having a high melting point (about 180° C.), which, however, has not yet been put into practical use as a binder resin as stated previously. Moreover, toner resins comprised of the conventional degradable polyester resin commonly have so poor a pulverizability that it is difficult for them to be used as binder resins which occupy 90% of toners of about 10 μm in particle diameter. Accordingly, taking account of their practical use as binder resins of toners, it has strongly been desired to improve their physical properties.

SUMMARY OF THE INVENTION

The present invention is to settle the subjects or problems discussed above. Accordingly, an object of the present invention is to provide a binder resin which can more highly contribute to the conservation of environment, and also which enables deinking with ease in a conventionally available deinking process making use of an alkali, to promote the reuse of copying paper having been used, and can satisfy various performances and properties required as toners, e.g., those concerning carrier-spent, fog, charging stability, running performance, storage stability, pulverizability, cost and so forth; a toner for developing electrostatic latent images which comprises such a binder resin; and an image-forming method and and an image-forming apparatus which make use of the toner.

The present inventors have made extensive studies in order to make development of a binder resin which can solve the problems discussed above and have superior properties. As the result, they have accomplished the present invention.

That is, the present invention provides a toner binder resin and a toner for developing electrostatic latent images which contains the binder resin, in which the binder resin is a toner binder resin comprising a polyhydroxyalkanoate (PHA) having at least two kinds of units, a 3-hydroxybutyrate (3HB) unit represented by the following formula (1) and a 3-hydroxyhexanoate (3HHx) unit represented by the following formula (2). The present invention also provides an image-forming method and an image-forming apparatus which make use of the toner.

(1): 3HB

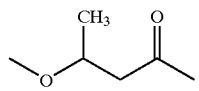

(2): 3HHx

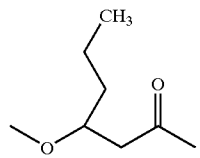

The present invention further provides a toner binder resin in which the above PHA is a PHA further containing at least one unit selected from a 4-hydroxybutyrate (4HB) unit represented by the following formula (3), a 4-hydroxyvalerate (4HV) unit represented by the following formula (4), a 3-hydroxyvalerate (3HV) unit represented by the following formula (5) and a 3-hydroxypropionate (3HP) unit represented by the following formula (6), a toner containing such a binder resin, and an image-forming method and an image-forming apparatus which make use of the toner.

(3): 4HB

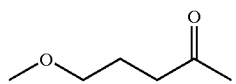

(4): 4HV

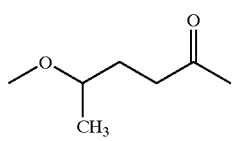

(5): 3HV

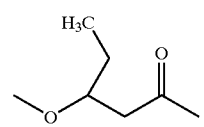

(6): 3HP

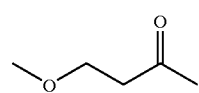

DETAILED DESCRIPTION OF THE PREFERRED EMBODIMENTS

Figure 1:
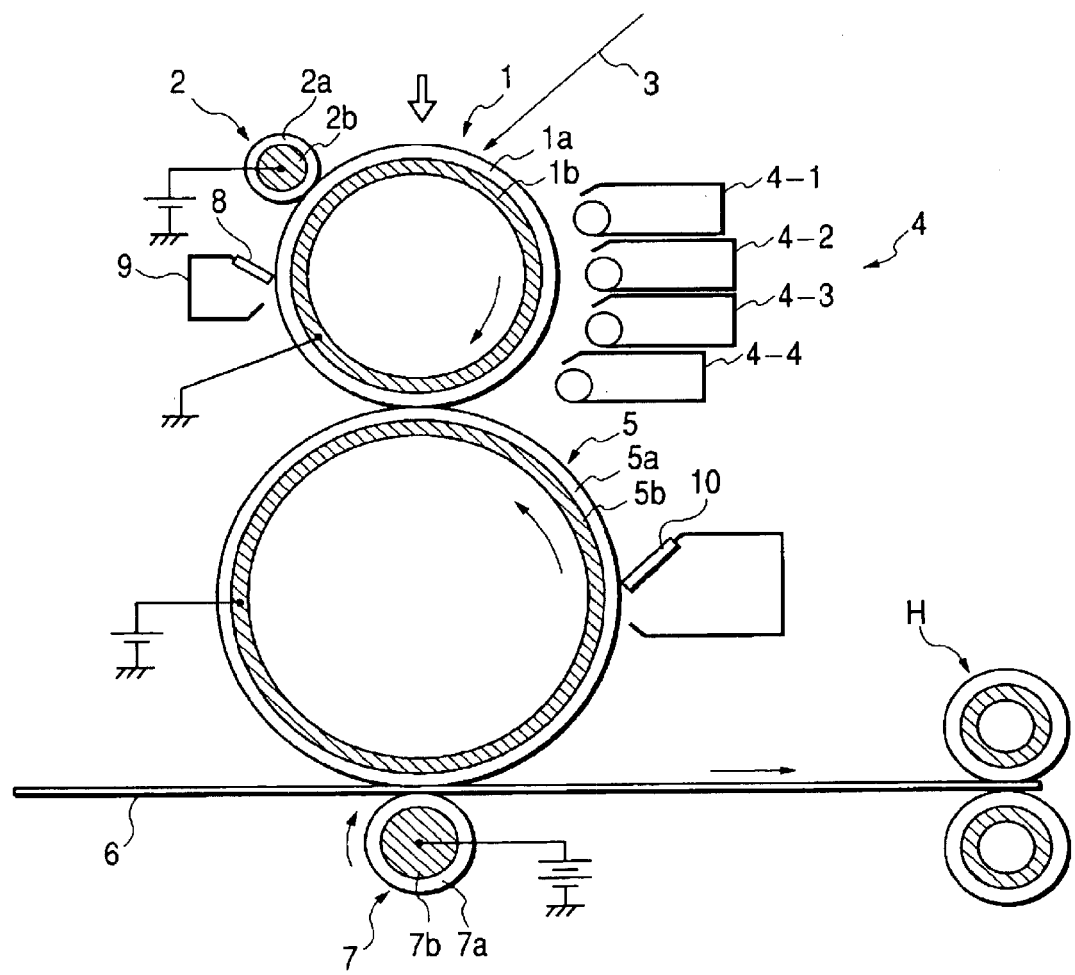
FIG. 1 is a schematic illustration of an image-forming apparatus used in Examples 27 to 42 and Comparative Examples 3 and 4.

The present invention is described below in detail by giving preferred embodiments.

In order to achieve the above objects, the present inventors have made extensive studies. As the result, we have discovered that a PHA comprised of two kinds of units, a 3-hydroxybutyrate (3HB) unit and a 3-hydroxyhexanoate (3HHx) unit at least, or a PHA comprising the above PHA which further contains at least one unit selected from a 4-hydroxybutyrate (4HB) unit, a 4-hydroxyvalerate (4HV) unit, a 3-hydroxyvalerate (3HV) unit and a 3-hydroxypropionate (3HP) unit has very good properties as a binder resin and has a high safety to human bodies and environment. We have also discovered that remarkable effects can be brought about when a toner for developing electrostatic latent images which contains such a binder resin is used and this toner for developing electrostatic latent images is used in image-forming apparatus having a certain development system. Thus, we have accomplished the present invention.

More specifically, the present invention is a binder resin comprising the PHA having two kinds of units, a 3-hydroxybutyrate (3HB) unit and a 3-hydroxyhexanoate (3HHx) unit at least, or the PHA comprising the above PHA which further contains at least one unit selected from a 4-hydroxybutyrate (4HB) unit, a 4-hydroxyvalerate (4HV) unit, a 3-hydroxyvalerate (3HV) unit and a 3-hydroxypropionate (3HP) unit, and is also a toner for developing electrostatic latent images which comprises such a binder resin. The present invention is further an image-forming method comprising a charging step of applying a voltage to a charging member from its outside to charge an electrostatic-latent-image-bearing member electrostatically; a developing step of developing an electrostatic latent image by the use of the above toner for developing electrostatic latent images, to form a toner image on the electrostatic-latent-image-bearing member; a transfer step of transferring to a transfer medium the toner image formed on the electrostatic-latent-image-bearing member via, or not via, an intermediate transfer member; and a heat fixing step of fixing by heat the toner image held on the transfer medium. The present invention is still further an image-forming apparatus comprising means corresponding to these steps of the method, i.e. a charging means, a developing means, a transfer means and a heat fixing means.

The binder resin of the present invention may also be a binder resin which further contains an additional biodegradable resin such as polycaprolactone or polylactic acid. The PHA may preferably have a number-average molecular weight of 300,000 or less because, in such molecular weight, it can have a good compatibility with the polycaprolactone or polylactic acid and a molten polymer blend which is colorless and transparent is obtainable. If on the other hand it has a relatively large number-average molecular weight of 500,000 or more, it can not have so good compatibility, and the resultant molten polymer blend may also have not a good hue. Even in such a case, however, the PHA can be improved in compatibility and the colorless and transparent, molten polymer blend can be obtained by mixing them under application of a high shear force to lower its molecular weight to 300,000 or less.

The binder resin of the present invention may also preferably have a number-average molecular weight of from 2,000 to 300,000. The binder resin of the present invention may further preferably have a glass transition point of from 30° C. to 80° C. and a softening point of from 60° C. to 170° C. in order for the function as a binder resin to be brought out.

Here, the PHA used in the present invention has a fundamental skeleton as a biodegradable resin. Hence, it has a high safety, and can be expected to have the effect of not affecting human bodies, environment and so forth. Also, like conventional plastic, the PHA can be utilized in the manufacture of various products by melting, and, different from synthetic polymers derived from petroleum, has a striking property that it can be broken down by microorganisms. Thus, when discarded, the PHA undergoes biodegradation and is taken into the circulation of substances in the natural world. Hence, it does not remain in the natural environment and does not cause any pollution while many synthetic polymeric compounds having conventionally been used have done, and also it has a high safety. Moreover, because of its biodegradable disposal, it does not require any disposal by combustion, and is an effective material also from the viewpoint of the prevention of air pollution and global warming. Thus, it can be utilized as a plastic which enables environmental safeguard. Also, the PHA is capable of being readily hydrolyzed in the presence of alkaline water. Hence, it has an advantage that toners containing coloring matter such as carbon black can effectively be removed from copied paper.

(PHA as Binder Resin)

The PHA, which is preferable as the binder resin used in the toner for developing electrostatic latent images according to the present invention, is specifically described below. The PHA used in the present invention is a polyester resin having 3-hydroxyalkanoates and/or 4-hydroxyalkanoates as monomer units. Here, where such a compound is produced by utilizing a microorganism, the polyester resin is an isotactic polymer consisting of only R-configuration. As long as the object of the present invention is achievable on both aspects of physical properties and function, it need not especially be the isotactic polymer. An atactic polymer may also be used. Also, the PHA may be obtained by a process of chemical synthesis in which a lactone compound is subjected to ring-opening polymerization using an organometallic catalyst (e.g., an organic catalyst containing aluminum, zinc, tin or the like).

Here, when the PHA of the present invention is produced by using a microorganism, it may contain the above various monomer units, or may be so designed that it may contain a suitable number of units, taking account of any necessary function characteristics, physical properties and so forth of the polymer. In general, the PHA may contain the above two to six kinds of monomer units, where it is expected that the object of the present invention can sufficiently be achieved. Where any delicate control of function characteristics and physical properties is intended, the PHA may also be constituted of more kinds of monomer units.

The PHA in the present invention may preferably have a glass transition point of from 30° C. to 80° C., particularly preferably from 40° C. to 80° C., and more preferably from 50° C. to 70° C. If it has a value lower than 30° C., a poor blocking resistance tends to result. If on the other hand it has a value higher than 80° C., a poor fixing performance tends to result. Also, the PHA in the present invention may preferably have a softening point of from 60° C. to 170° C., and particularly preferably from 80° C. to 140° C. If it has a softening point lower than 60° C., a lowering of anti-offset properties may be seen. If it has a softening point higher than 170° C., a higher fixing temperature tends to result.

The PHA having these desired physical properties may be obtained by selecting conditions for culturing any microorganism capable of synthesizing the PHA in the present invention. For example, its number-average molecular weight may be controlled by controlling culturing time and so forth. Its number-average molecular weight may also be controlled by removing low-molecular-weight components by means of solvent extraction, re-precipitation or the like. Here, the glass transition point and softening point have correlation with the molecular weight of the PHA. Also, the glass transition point and softening point may be controlled by controlling the type and compositional ratio of the monomer units in the PHA.

The PHA in the present invention may preferably have a weight-average molecular weight Mw of from 4,000 to 600,000, and may preferably have a number-average molecular weight Mn of from 2,000 to 300,000, and particularly preferably from 5,000 to 150,000. If it has an Mn of less than 2,000, the PHA may have a greatly low glass transition point, resulting in a poor blocking resistance. If on the other hand it has an Mn of more than 300,000, the PHA may come highly viscous at the time of melting, resulting in a poor fixing performance.

Biosynthesis of PHA

With regard to methods of synthesizing the PHA used in the present invention, any known method may be used. For example, methods disclosed in Japanese Patent Applications Laid-open No. 05-093049, No. 07-082352, No. 07-265065, No. 08-289797, No. 09-020857, No. 09-087499 and so forth. Also, as methods of collecting the PHA according to the present invention from the bacterial body of a microorganism, those disclosed in Japanese Patent Applications Laid-open No. 2001-046094, No. 2001-057895 and so forth may preferably be used.

Where microorganisms are utilized in the production of PHAs used in the binder resin of the present invention, there are no particular limitations on microorganisms usable for the production as long as they are microorganisms capable of accumulating any PHA in cells. For example, they may include microorganisms belonging to the genus *Alcaligenes* such as *Alcaligenes lipolytica, Alcaligenes eutrophus* and *Alcaligenes latus*, the genus *Pseudomonas*, the genus *Bacillus*, the genus *Azotobacter*, the genus *Nocardia* and the genus *Aeromonas*. In particular, strains of *Aeromonas caviae* or the like, strains into which genes of PHA-synthesizing enzymes derived from *Aeromonas caviae* have been introduced, as exemplified by *Alcaligenes eutrophus* strain A32C (Deposition No. FERM P-15786), may be used. There are also no particular limitations on methods of culturing these microorganisms as long as the PHA can be accumulated in the bacterial body in a large quantity and in a good efficiency. For example, in the case when the *Alcaligenes eutrophus* strain A32C (FERM P-15786) is used, the method described in J. Bacteriol., 179, pp.4821–4880 (1997) may be used.

For example, as disclosed in Japanese Patent Application Laid-open No. 05-093049, a copolymer P(3HB-CO-3HHx)

containing C4(3HB):C6(3HHx)=70 to 90:30 to 10 may be obtained only by supplying as a carbon source a fatty acid having 6 or more even-number carbon atoms, or a lower-alcohol ester thereof, or, as in the case where natural fats and oils are used as a carbon source, fats and oils (vegetable oil and fish oil) most abundantly naturally present, to a microorganism of the genus *Aeromonas* to effect culturing aerobically under restriction of nutrient sources other than the carbon source, usually under restriction of a nitrogen source. Where it is intended to make the C6 unit compositionally higher, caproic acid or β-hydroxycaproic acid may be made coexistent as a carbon source. Also, where it is intended to make the C4 unit compositionally higher, butyric acid or β-hydroxybutyric acid may be made coexistent. As the result, the composition can be controlled up to C4(3HB):C6 (3HHx)=50 to 98:50 to 2.

Here, as the natural fats and oils, at least one of cone oil, soybean oil, safflower oil, sunflower oil, olive oil, coconut oil, palm oil, rapeseed oil, fish oil, whale oil, lard and beef tallow may be used. Also, P(3HB-CO-3HHx-CO-4HB) may also be synthesized using as a carbon source a mixture of a long-chain fatty acid and 4-hydroxybutyric acid.

As a further example, where the fatty acid having 6 or more even-number carbon atoms, or a lower-alcohol ester thereof, or any of natural fats and oils is used as a carbon source as in the foregoing, a three-component type copolymer P(3HB-CO-3HV-CO-3HHx) in which a (C4+C6) unit and a C5 unit are arbitrarily controllable in terms of the ratio thereof may be obtained by making up a copolymer comprised of C4 and C6 two units, utilizing the nature that a polyester comprised only of C5 is produced from valeric acid (a C5 fatty acid), and supplying a mixed carbon source consisting of the fatty acid having 6 or more even-number carbon atoms and valeric acid (or a fatty acid having 5 or more odd-number carbon atoms). Also, a three-component type copolymer P(3HB-CO-3HP-CO-3HHx) in which a (C4+C6) unit and a C3 unit are arbitrarily controllable in terms of the ratio thereof may be obtained when propionic acid (a C3 fatty acid) is supplied in place of the valeric acid.

Like the case of the above three-component type copolymers, as carbon sources to the microorganism of the genus *Aeromonas*, in addition to the fatty acid having 6 or more even-number carbon atoms, or a lower-alcohol ester thereof, or any of natural fats and oils, a mixed carbon source may be supplied which make use of any two kinds selected from 5-chlorovaleric acid or propionic acid, a fatty acid having 5 or more odd-number carbon atoms, and 4-hydroxybutyric acid or γ-butylolactone, whereby a four-component type copolymer can be synthesized which is comprised of a four-component type monomer unit containing a 3-hydroxybutyrate (3HB) unit and a 3-hydroxyhexanoate (3HHx) unit and further any two units selected from a 3-hydroxypropionate (3HP) unit, a 3-hydroxyvalerate (3HV) unit, a 4-hydroxybutyrate (4HB) unit and a 4-hydroxyvalerate (4HV) unit, which correspond to the respective additional carbon sources.

As also disclosed in the above Japanese Patent Application Laid-open No. 08-289797, those which are preferably usable in the present invention, e.g., the three-component type copolymers have wide properties that they simultaneously have the characteristic features of the 3HB-3HV and 3HB-3HHx two-component type copolymers as polymer's physical properties. Hence, they can be controlled to have optimum composition in accordance with uses. More specifically, P(3HB-CO-3HV) is a highly crystalline copolymer having a crystallinity of from 50% to 70%, which forms a 3HB type crystal structure when it has large 3HB composition and which has a 3HV type crystal structure when it has large 3HV composition. P(3HB-CO-3HHx) is a copolymer in which the 3HHx is not incorporated in the crystal structure and which decreases in crystallinity with an increase in 3HHx composition. In such two-component type copolymers, it is difficult to control their melting point, glass transition point, tensile strength and elongation while controlling the crystallinity. However, the three-component type copolymer P(3HB-CO-3HV-CO-3HHx) is a material rich in utility in view of an advantage that it is possible to control these.

As the polylactic acid, which may further be added to and used in the PHA in the present invention, commercially available one, e.g., LACTY (trade name; available from Shimadzu Corporation) may preferably be used, and besides those obtained by various polymerization processes may be used.

Other Constituent Materials

Other constituent materials which constitute the toner for developing electrostatic latent images according to the present invention are described below. The toner for developing electrostatic latent images is constituted of, in addition to the binder resin described above, a colorant, a charge control agent and other additives which are optionally added.

Additional Binder Resin

First, as the binder resin, the binder resin of the present invention may preferably be used. In addition to the binder resin of the present invention, other thermoplastic resin may be incorporated as a binder resin. For example, the former may be used in the form of its mixture with one or more of polymers such as polystyrene, polyacrylate and a styrene-acrylate copolymer, polyvinyl chloride, polyvinyl acetate, polyvinylidene chloride, phenolic resins, epoxy resins and polyester resins, and any resins may be used without any particular limitations as long as they are those usually used when toners are produced.

Where a thermoplastic resin having no biodegradability is used as the binder resin other than the PHA, such an additional thermoplastic resin may preferably be mixed in a proportion of 80% by weight or less, and particularly 50% by weight or less based on the total weight of the binder resin. If the additional thermoplastic resin is in a proportion larger than 80% by weight, the additional thermoplastic resin may have so excessively a high binding strength to the paper surface that the toner may have low deinking properties. Also, where the toner is used as a biodegradable toner, it is preferable not to mix such an additional thermoplastic resin having no biodegradability.

In the present invention, any commercially available biodegradable plastic of various types may also preferably be mixed and used. The biodegradable plastic may include, e.g., ECOSTAR and ECOSTAR PLUS (trade names; available from Hagiwara Kogyo), BIOPOL (trade name; available from I.C.I Japan), AJICOAT (trade name; available from Ajinomoto), PLACCEL and POLYCAPROLACTONE (trade names; available from Daicell Chemical), SHOLEX and BIONOLLE (trade names; available from Showa Denko), LACTY (trade name; available from Shimadzu Corporation), and LACEA (trade name; available from Mitsui Chemical). In the case when any of these resins are mixed and used, the biodegradability inherent in the toner of the present invention is not damaged.

Of these, the polycaprolactone (i.e., a polymer of ε-caprolactone) or the polylactic acid referred to previously is particularly preferred in view of advantages that it is completely degradable with ease by lipase, esterase or the like and it can readily be blended with other resins, or modified in physical properties by copolymerization or the like.

The styrene type polymers may include copolymers of styrene with acrylate or methacrylate and copolymers of other monomers copolymerizable with these, and copolymers of styrene with diene monomers (such as butadiene and isoprene) and copolymers of other monomers copolymerizable with these. The polyester type polymers may include polycondensation products of aromatic dicarboxylic acids with alkylene oxide addition products of aromatic diols. The epoxy type polymers may include reaction products of aromatic diols with epichlorohydrin, and modified products thereof. The polyolefin type polymers may include polyethylene, polypropylene, and copolymers of any of these with other copolymerizable monomers. The polyurethane type polymers may include polyaddition products of aromatic diisocyanates with alkylene oxide addition products of aromatic diols.

As specific examples of the binder resin usable in the form of a mixture with the binder resin of the present invention, it may include polymers of the following polymerizable monomers, or mixtures of any of these, or copolymerization products obtained using two or more of the following polymerizable monomers. Such resins may specifically include, e.g., styrene type polymers such as styrene-methacrylic acid type polymers, as well as the polyester type polymers, epoxy type polymers, polyolefin type polymers and polyurethane type polymers.

As specific examples of the polymerizable monomers, they may include, e.g., styrene; styrene derivatives such as o-methylstyrene, m-methylstyrene, p-methylstyrene, p-methoxystyrene, p-phenylstyrene, p-chlorostyrene, 3,4-dichlorostyrene, p-ethylstyrenee, 2,4-dimethylstyrene, p-n-butylstyrene, p-tert-butylstyrene, p-n-hexylstyrene, p-n-octylstyrene, p-n-nonylstyrene, p-n-decylstyrene and p-n-dodecylstyrene; ethylene unsaturated monoolefins such as ethylene, propylene, butylene and isobutylene; unsaturated polyenes such as butadiene; vinyl halides such as vinyl chloride, vinylidene chloride, vinyl bromide and vinyl fluoride; vinyl esters such as vinyl acetate, vinyl propionate and vinyl benzoate; α-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate and diethylaminoethyl methacrylate; acrylic esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate and phenyl acrylate; vinyl ethers such as methyl vinyl ether, ethyl vinyl ether and isobutyl vinyl ether; vinyl ketones such as methyl vinyl ketone, hexyl vinyl ketone and methyl isopropenyl ketone; N-vinyl compounds such as N-vinylpyrrole, N-vinylcarbazole, N-vinylindole and N-vinylpyrrolidone; vinylnaphthalenes; acrylic acid or methacrylic acid derivatives such as acrylonitrile, methacrylonitrile and acrylamide; esters of the above α,β-unsaturated acids and diesters of dibasic acids; dicaroxylic acids such as maleic acid, methyl maleate, butyl maleate, dimethyl maleate, phthalic acid, succinic acid and terephthalic acid; polyol compounds such as ethylene glycol, diethylene glycol, triethylene glycol, 1,2-propyleneglycol, 1,3-propyleneglycol, 1,4-butanediol, 1,6-hexanediol, bisphenol A, hydrogenated bisphenol A and polyoxyethylene type bisphenol A; isocyanates such as p-phenylenediisocyanate, p-xylylenediisocyanate and 1,4-tetramethylenediisocyanate; amines such as ethylamine, butylamine, ethylenediamine, 1,4-diaminobenzene, 1,4-diaminobutane and monoethanolamine; and epoxy compounds such as diglycidyl ether, ethylene glycol diglycidyl ether, bisphenol-A diglycidyl ether and hydroquinone diglycidyl ether.

(Cross-linking Agent)

When the binder resin usable in the form of a mixture with the binder resin of the present invention is made up, a cross-linking agent as shown below may optionally be used.

For example, it may include, as bifunctional cross-linking agents, divinylbenzene, bis(4-acryloxypolyethoxyphenyl) propane, ethylene glycol diacrylate, 1,3-butyleneglycoldiacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates (MANDA, trade name; available from Nippon Kayaku Co., Ltd.), and the above diacrylates whose acrylate moiety has been replaced with methacrylate.

As trifunctional or more, polyfunctional cross-linking agents it may include, e.g., pentaerythritol triacrylate, trimethylolethane triacrylate, trimethylolpropane triacrylate, tetramethylolmethane tetraacrylate, oligoester acrylate, and these compounds whose acrylate moiety has been replaced with methacrylate, and also 2,2-bis(4-methacyloxypolyethoxyphenyl)propane, diallyl phthalate, triallyl cyanurate, triallyl asocyanurate triallyl isocyanurate, triallyl trimellitate and diaryl chlorendate.

(Polymerization Initiator)

When the binder resin usable in the form of a mixture with the binder resin of the present invention is made up, a polymerization initiator as shown below may also optionally be used.

For example, it may include t-butyl peroxy-2-ethylhexanoate, cumin perpivalate, t-butyl peroxylaurate, benzoyl peroxide, lauroyl peroxide, octanoyl peroxide, di-t-butyl peroxide, t-butylcumyl peroxide, dicumyl peroxide, 2,2'-azobis(2-isobutyronitrile), 2,2'-azobis(2-methylbutyronitrile), 2,2'-azobis(2,4-dimethylvaleronitrile), 2,2'-azobis(4-methoxy-2,4-dimethylvaleronitrile), 1,1-bis(t-butylperoxy)-3,3,5-trimethylcyclohexane, 1,1-bis(t-butylperoxy)cyclohexane, 1,4-bis(t-butylperoxycarbonyl) cyclohexane, 2,2-bis(t-butylperoxy)octane, n-butyl-4,4-bis (t-butylperoxy) valylate, 2,2-bis(t-butylperoxy)butane, 1,3-bis(t-butylperoxy-isopropyl)benzene, 2,5-dimethyl-2,5-di(t-butylperoxy)hexane, 2,5-dimethyl-2,5-di(t-butylperoxy) hexane, 2,5-dimethyl-2,5-di(benzoylperoxy)hexane, di-t-butyl peroxyisophthalate, 2,2-bis(4,4-di-t-butylperoxycyclohexyl)propane, di-t-butylperoxy-α-methylsuccinate, di-t-butyl peroxydimethylglutarate, di-t-butyl peroxyhexahydroterephthalate, di-t-butyl peroxyazelate, 2,5-diemthyl-2,5-di(t-butylperoxy)hexane, diethylene glycol-bis(t-butylperoxycarbonate), di-t-butyl peroxytrimethyladipate, tris(t-butylperoxy)triazine and vinyl tris(t-butylperoxy)silane. Any of these may used alone or in combination. The initiator may be used in an amount of not less than 0.05 part by weight, and preferably from 0.1 part by weight to 15 parts by weight, based on 100 parts by weight of the monomer.

(Colorant)

As the colorant that constitutes the toner for developing electrostatic latent images according to the present invention, any colorants may be used without any particular limitations as long as they are those usually used when toners are produced. All pigments and/or dyes maybe used, as exemplified by carbon black, titanium white, monoazo type red pigments, disazo type yellow pigments, quinacridone type magenta pigments and anthraquinone type dyes.

Stated more specifically, when the toner for developing electrostatic latent images according to the present invention is used as a magnetic color toner, the colorant may include, e.g., C.I. Direct Red 1, C.I. Direct Red 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4 and C.I. Basic Green 6. As the pigments, usable are chrome yellow, cadmium yellow, mineral fast yellow, navel yellow, Naphthol Yellow S, Hanza Yellow G, Permanent Yellow NCG, Tartrazine Yellow Lake, chrome orange, molybdenum orange, Permanent Orange GTR, Pyrazolone Orange, Benzidine Orange G, cadmium red, Permanent Red 4R, Watching Red calcium salt, Eosine Lake, Brilliant Carmine 3B, manganese violet, Fast Violet B, Methyl Violet Lake, Prussian blue, cobalt blue, Alkali Blue Lake, Victoria Blue Lake, Phthalocyanine Blue, Fast Sky Blue, Indanthrene Blue BC, chrome green, chromium oxide, Pigment Green B, Malachite Green Lake, Final Yellow Green G and so forth.

When the toner for developing electrostatic latent images according to the present invention is used as toners for full-color two-component developers, those shown below may be used as colorants. For example, color pigments for a magenta toner may include, C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209; C.I. Pigment Violet 19; and C.I. Vat Red 1, 2, 10, 13, 15, 23, 29, 35.

In the present invention, any of the pigments listed above may be used alone, or dyes may be used in combination with such pigments so that color sharpness can be improved. This is preferable in view of image quality of full-color images. Magenta dyes usable in such a case may include oil-soluble dyes such as C.I. Solvent Red 1, 3, 8, 23, 24, 25, 27, 30, 49, 81, 82, 83, 84, 100, 109, 121, C.I. Disperse Red 9, C.I. Solvent Violet 8, 13, 14, 21, 27, and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39, 40, and C.I. Basic Violet 1, 3, 7, 10, 14, 15, 21, 25, 26, 27, 28.

As other color pigments, cyan color pigments may include C.I. Pigment Blue 2, 3, 15, 16, 17, C.I. Vat Blue 6, C.I. Acid Blue 45, or copper phthalocyanine pigments whose phthalocyanine skeleton has been substituted with 1 to 5 phthalimide methyl group(s).

Yellow color pigments may include C.I. Pigment Yellow 1, 2, 3, 4, 5, 6, 7, 10, 11, 12, 13, 14, 15, 16, 17, 23, 65, 73, 83, and C.I. Vat Yellow 1, 3, 20.

The dyes and pigments as described above may each be used alone. Otherwise, any of them may arbitrarily be mixed and then used, in order to obtain the desired color tone of toners.

Taking account of the environmental conservation and the safety to human bodies, water-insoluble food dyes such as food lakes of various types may preferably be used, which may include, e.g., food red No. 40 aluminum lake, food red No. 2 aluminum lake, food red No. 3 aluminum lake, food red No. 106 aluminum lake, food yellow No. 5 aluminum lake, food yellow No. 4 aluminum lake, food blue No. 1 aluminum lake and food blue No. 2 aluminum lake.

The above water-insoluble food dyes may also function as charge control agents. In such a case, as charge control agents for negative charging, the above aluminum lakes may preferably be used. Thus, in the case when the water-insoluble food dyes have the function of charge control agents, they not only can improve the environmental safety of toners, but also can contribute to the cost reduction of toners.

The content of the above colorant in the toner may be changed in a wide range in accordance with the desired coloring effect and so forth. Usually, in order to attain the best toner characteristics, i.e., taking account of coloring power for printing, shape stability of toner particles, toner scattering and so forth, any of these colorants may usually be used in an amount of from 0.1 to 60 parts by weight, and preferably from 0.5 to 20 parts by weight, based on 100 parts by weight of the binder resin.

Other Constituents of Toner (Charge Control Agent)

As the charge control agent, any charge control agent used conventionally may be used. As specific examples, it may include nigrosine type dyes and quaternary ammonium salt or monoazo type metal complex salt dyes. The quantity of the charge control agent to be used may be determined taking account of conditions such as the chargeability of the binder resin, the quantity of the colorant to be added, the method of production inclusive of a dispersion method and the chargeability of other additives. The charge control agent may be used in a proportion of from 0.1 to 20 parts by weight, and preferably from 0.5 to 10 parts by weight, based on 100 parts by weight of the binder resin. Besides this, inorganic particles such as metal oxide particles or an inorganic material surface-treated with an organic material may also be used. Any of these charge control agents may be so used as to be mixed in the binder resin, or may be used in such a form that it has adhered to toner particle surfaces.

In the toner for developing electrostatic latent images according to the present invention, in addition to the binder resin and colorant components described above, the following compounds may be added. Such compounds are exemplified by silicone resin, polyester, polyurethane, polyamide, epoxy resin, polyvinyl butyral, rosin, modified rosin, terpene resin, phenolic resin, aliphatic hydrocarbon resin such as low-molecular weight polyethylene or low-molecular weight polypropylene or alicyclic hydrocarbon resin, aromatic petroleum resin and chlorinated paraffin or paraffin wax. Waxes preferably usable among these may specifically include low-molecular weight polypropylene and by-products thereof, low-molecular weight polyester, ester waxes, and aliphatic derivatives. Waxes obtained from these waxes by fractionating the waxes by various methods may also preferably be used. Also, after the fractionation, the waxes may be subjected to oxidation, block copolymerization or graft modification.

In the toner for developing electrostatic latent images according to the present invention, a toner having superior performance can be obtained especially when it contains the above wax component and such a wax component stands dispersed in the binder resin in the form of spherical and/or spindle-shaped islands in its cross-sectional observation of toner particles using a transmission electron microscope (TEM).

Toner Production Process

As a specific process for producing the toner for developing electrostatic latent images according to the present invention, constituted as described above, any conventionally known process may be used. The toner for developing electrostatic latent images according to the present invention may be produced by, e.g., what is called a pulverization process, which produces the toner according to the following steps.

That is, stated specifically, resins such as the binder resin of the present invention, and other components such as the charge control agent and the wax which are optionally added are thoroughly mixed by means of a mixing machine such as a Henschel mixer or a ball mill, and then the mixture is melt-kneaded using a heat kneading machine such as a heating roll, a kneader or an extruder to make the resin and so on melt one another, in which the pigment, dye or magnetic material as the colorant and additives such as a metal compound optionally added are then dispersed or dissolved, followed by cooling for solidification. Thereafter, the solidified product is pulverizes by means of a grinding machine such as a jet mill or a ball mill, followed by classification. Thus, the toner for developing electrostatic latent images according to the present invention, having the desired particle diameter, can be obtained. Incidentally, in the step of classification, a multi-division classifier may preferably be used in view of production efficiency.

The toner for developing electrostatic latent images according to the present invention, having the desired particle diameter, may also be obtained by mixing the binder resin and the charge control agent in the form of a solution using a solvent (including aromatic hydrocarbons such as toluene and xylene, halogenated products such as chloroform and ethylene dichloride, ketones such as acetone and methyl ethyl ketone, and amides such as dimethylformamide), stirring the solution, and thereafter introducing the resultant solution into water to effect reprecipitation, followed by filtration and then drying, and thereafter pulverizing the solidified product by means of a grinding machine such as a jet mill or a ball mill, followed by classification. Incidentally, in the step of classification, a multi-division classifier may preferably be used in view of production efficiency.

The toner for developing electrostatic latent images according to the present invention may still also be produced by what is called a polymerization process as described below. That is, in this case, materials such as a polymerizable monomer of the binder resin according to the present invention, the pigment, dye or magnetic material as the colorant, and optionally the cross-linking agent, the polymerization initiator, the wax and other additives are mixed and dispersed to prepare a polymerizable monomer composition, which is then subjected to suspension polymerization in an aqueous dispersion medium to synthesize polymerized color resin particles. The resin particles thus obtained are solid-liquid separated, followed by drying and then optionally classification to obtain the toner for developing electrostatic latent images according to the present invention.

(Silica External Additive)

In the present invention, to the toner produced by the process as described above, it is preferable to add a fine silica powder in order to improve toner's charging stability, fluidity and running performance. As the fine silica powder used here, a fine silica powder having a specific surface area of 20 $m^2/g$ or more, and particularly in the range of from 30 to 400 $m^2/g$, as measured by nitrogen adsorption according to the BET method, gives good results. In this case, the fine silica powder may be used in an amount of from 0.01 to 8 parts by weight, and preferably from 0.1 to 5 parts by weight, based on 100 parts by weight of the toner particles. For the purpose of making hydrophobic treatment and controlling chargeability, the fine silica powder used here may preferably optionally be treated with a treating agent such as a silicone varnish, a modified silicone varnish of various types, a silicone oil, a modified silicone oil of various types, a silane coupling agent, a silane coupling agent having a functional group or other organosilicon compound. Use of such a treated powder is preferred. Any of these treating agents may be used in the form of a mixture.

(Inorganic Powder)

In order to improve toner's developing performance and running performance, it is also preferable to add the following inorganic powder. It may include, e.g., oxides of metals such as magnesium, zinc, aluminum, cerium, cobalt, iron, zirconium, chromium, manganese, strontium, tin and antimony; composite metal oxides such as calcium titanate, magnesium titanate and strontium titanate; metal salts such as calcium carbonate, magnesium carbonate and aluminum carbonate; clay minerals such as kaolin; phosphoric acid compounds such as apatite; silicon compounds such as silicon carbide and silicon nitride; and carbon powders such as carbon black and graphite powder. In particular, fine powder of zinc oxide, aluminum oxide, cobalt oxide, manganese dioxide, strontium titanate or magnesium titanate may preferably be used.

(Lubricant)

A lubricant powder as shown below may also be added to the toner. It may include, e.g., fluorine resins such as Teflon and polyvinylidene fluoride; fluorine compounds such as carbon fluoride; fatty acid metal salts such as zinc stearate; fatty acids, and fatty acid derivatives such as fatty esters; and molybdenum sulfide.

These constituents, the binder resin usable in the form of a mixture with the binder resin of the present invention, colorant, charge control agent and other additives optionally added, are each in a very small content in the toner. However, taking account of post-disposal, it is more preferable to use those having biodegradability.

The toner for developing electrostatic latent images according to the present invention, constituted as described above, may be used alone as a non-magnetic one-component developer, or may be applied to conventionally known various toners such as a non-magnetic toner which constitutes a magnetic two-component developer together with a magnetic carrier, and a magnetic toner used alone as a magnetic one-component developer. Here, as a carrier used in two-component development, any of conventionally known carriers may be used. Stated specifically, particles formed of metals such as iron, nickel, cobalt, manganese, chromium and rare earth elements, and alloys or oxides thereof, having been surface-oxidized or unoxidized and having an average particle diameter of from 20 to 300 $\mu m$, may be used. Also, it is preferable to use carriers comprising such carrier particles to or on the surfaces of which a material such as a styrene resin, an acrylic resin, a silicone resin, a fluorine resin or a polyester resin has been made to adhere or coated.

Magnetic Toner

The toner for developing electrostatic latent images according to the present invention may also be made usable as a magnetic toner by incorporating a magnetic material into toner particles. In this case, the magnetic material may also be made to serve as the colorant. The magnetic material used here may include iron oxides such as magnetite, hematite and ferrite; magnetic metals such as iron, cobalt and nickel, or alloys of any of these metals with a metal such as aluminum, cobalt, copper, lead, magnesium, tin, zinc, antimony, beryllium, bismuth, cadmium, calcium, manganese, selenium, titanium, tungsten or vanadium, and mixtures of any of these. As these magnetic material usable in the present invention, those having an average particle diameter of from 2 $\mu m$ or less, and preferably approximately from 0.1 to 0.5 µm, are preferred. As its quantity in which it is incorporated in the toner, it may preferably be used in an amount of from 20 to 200 parts by weight based on 100 parts by weight of the binder resin, and particularly in an amount of from 40 to 150 parts by weight based on 100 parts by weight of the binder resin.

In order to achieve much higher image quality, it must be made possible to develop finer latent image dots faithfully. For that end, it is preferable that, e.g., the toner for developing electrostatic latent images according to the present invention has toner particles so regulated as to have a weight-average particle diameter of from 4 µm to 9 µm. Namely, toner particles having a weight-average particle diameter smaller than 4 µm are not preferable because they may cause a lowering of transfer efficiency and hence transfer residual toner tends to remain on the photosensitive member in a large quantity, tending to cause non-uniform or uneven images due to fog and faulty transfer. Also, toner particles having a weight-average particle diameter larger than 9 µm tend to cause spots around characters or line images.

The toner for developing electrostatic latent images according to the present invention may preferably have a charge quantity (two-component method) per unit weight, of from −10 to −80 µC/g, and more preferably from −15 to −70 µC/g. This is preferable in order to improve transfer efficiency in a transfer method making use of a transfer member to which a voltage is kept applied.

In the present invention, the average particle diameter and particle size distribution of the toner are measured with a Coulter counter Model TA-II or Coulter Multisizer (manufactured by Coulter Electronics, Inc.). An interface (manufactured by Nikkaki k.k.) that outputs number distribution and volume distribution and a personal computer PC9801 (manufactured by NEC.) are connected. As an electrolytic solution used in the measurement, an aqueous 1% NaCl solution is prepared using first-grade sodium chloride. For example, commercially available, ISOTON R-II (available from Coulter Scientific Japan Co.) may be used. As a specific method, measurement is made by adding as a dispersant from 0.1 to 5 mL of a surface active agent (preferably an alkylbenzene sulfonate) to from 100 to 150 ml of the above aqueous electrolytic solution, and further adding from 2 to 20 mg of a sample to be measured. The electrolytic solution in which the sample has been suspended is subjected to dispersion for about 1 minute to about 3 minutes in an ultrasonic dispersion machine. The volume distribution and number distribution are calculated by measuring the volume and number of toner particles with particle diameters of not smaller than 2 µm by means of the above Coulter counter Model TA-II, using an aperture of 100 µm as its aperture. Then the values according to the present invention are determined, which are the volume-based, weight-average particle diameter (D4) determined from the volume distribution and the number-based, number-average particle diameter (D1) determined from number distribution.

Charge Quantity

Figure 7:
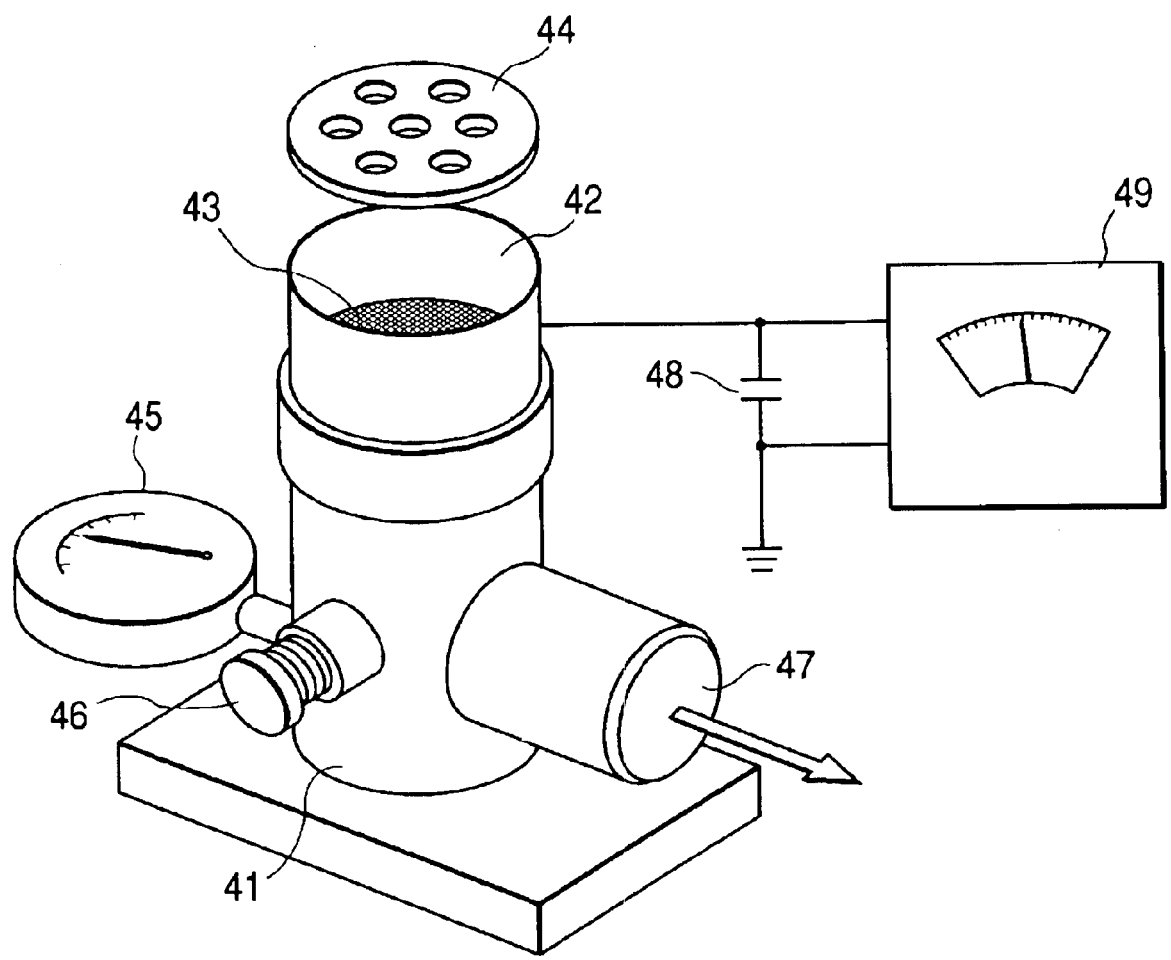
FIG. 7 is a diagrammatic illustration of a blow-off charge quantity measuring unit with which the charge quantity of toners is measured.

A method of measuring the charge quantity (two-component triboelectricity) by the two-component method used in the present invention is described below. In the measurement, a charge quantity measuring device shown in FIG. 7 is used. First, in a fixed environment and using an iron powder EFV200/300 (available from Powder Teck Co.) as the carrier, a mixture prepared by adding 0.5 g of the measuring-object toner to 9.5 g of the carrier is put in a bottle with a volume of 50 to 100 mL, made of polyethylene, and is set on a shaker having a fixed shaking width, followed by shaking for a fixed time, setting shaking conditions at a shaking width of 100 mm and a shaking speed of 100 to-and-fro times per minute. Then, 1.0 to 1.2 g of the resulting mixture is put in a measuring container 42 made of a metal at the bottom of which a screen 43 of 20 µm mesh (500 meshes) is provided, and the container is covered with a plate 44 made of a metal. The total weight of the measuring container 42 at this time is weighed and is expressed as W1 (g). Next, in a suction device (not shown; made of an insulating material at least at the part coming into contact with the measuring container 42), air is sucked from a suction opening 47 and an air-flow control valve 46 is operated to control the pressure indicated by a vacuum indicator 45 to be 2,450 Pa (250 mmAq). In this state, suction is carried out for one minute to remove the toner by suction. The potential indicated by a potentiometer 49 at this time is expressed as V (volt). Herein, numeral 48 denotes a capacitor, whose capacitance is expressed as C (µF). The total weight of the measuring container after completion of the suction is also weighed and is expressed as W2 (g). The quantity of triboelectricity (µC/g) of the toner is calculated from these measured values according to the following expression.

Quantity of triboelectricity $(\mu C/g)=C \times V/(W1-W2)$

Molecular Weight Distribution of Binder Resin

In the present invention, the molecular weight of the binder resin is measured by GPC (gel permeation chromatography). As a specific method for measurement by GPC, a sample obtained by beforehand subjecting the toner to extraction with a THF (tetrahydrofuran) solvent for 20 hours by means of a Soxhlet extractor is used for the measurement. As column constitution, A-801, A-802, A-803, A-804, A-805, A-806 and A-807, available from Showa Denko K.K., are connected, and the molecular weight distribution is measured using a calibration curve of standard polystyrene resin.

In the present invention, it is also preferable to use as the binder resin a binder resin having a ratio of weight-average molecular weight (Mw) to number-average molecular weight (Mn), Mw/Mn, of from 2 to 100, as measured in the manner as described above.

Glass Transition Point of Toner

It is further preferable for the toner of the present invention to be so prepared as to have a glass transition point Tg of from 30° C. to 80° C., and more preferably from 50° C. to 70° C., in view of fixing performance and storage stability. The glass transition point Tg in this case may be measured with, e.g., a differential scanning calorimeter of a highly precise, inner-heat input compensation type, such as DSC-7, manufactured by Perkin-Elmer Corporation. It is measured according to ASTM D3418-82. In the present invention, a measuring sample is once heated to take a previous history and thereafter cooled rapidly. Then, the sample is again heated at a heating rate of 10° C./min. within the temperature range of 0 to 200° C., where the DSC curve thus measured may be used.

Image-Forming Method and Apparatus

The toner for developing electrostatic latent images according to the present invention, constituted as described above, may particularly preferably be applied to;

an image-forming method having at least a charging step of applying a voltage to a charging member from its outside to charge an electrostatic-latent-image-bearing member electrostatically; a latent-image-forming step of forming an electrostatic latent image on the electrostatic-latent-image-bearing member thus charged; a developing step of developing the electrostatic latent image by the use of a toner to form a toner image on the electrostatic-latent-image-bearing member; a transfer step of transferring to a recording medium the toner image formed on the electrostatic-latent-image-bearing member; and a heat fixing step of fixing by heat the toner image held on the recording medium; or an image-forming method in which the transfer step comprises a first transfer step of transferring to an intermediate transfer member the toner image formed on the electrostatic-latent-image-bearing member and a second transfer step of transferring to a recording medium the toner image held on the intermediate transfer member.

The apparatus used in this method may preferably have means corresponding to the respective steps, i.e., a charging means, an electrostatic-latent-image-forming means, a developing means, a transfer means and a heat fixing means.

EXAMPLES

The present invention is described below in greater detail by giving Examples and Comparative Examples. Also, "part (s)" in the following formulation is "part(s) by weight" in all occurrences.

Example 1

A PHA was produced using *Aeromonas caviae* strain FA-440 (FERM BP-3432).

In 20 L of a culture medium shown below, the strain FA-440 was inoculated to effect shaking culture at 30° C. for 24 hours. More specifically, to a mixture having the following culture medium composition, water was added to make the mixture 1 liter in total amount (pH: 7.0) to prepare the culture medium, and the strain was inoculated therein.

| | | |
|---|---|---|
| Meat extract | 5 g | |
| Polypeptone | 10 g | |
| Yeast extract | 10 g | |
| $KH_2PO_4$ | 0.5 g | |
| $K_2HPO_4$ | 0.5 g | |
| $MgSO_4.7H_2O$ | 0.1 g | |

After the culturing was completed, the resultant culture solution was put to centrifugation to collect the bacterial body, and further the bacterial body was added in its entirety to 20 L of a culture medium shown below to effect shaking culture at 30° C. for 24 hours. More specifically, to a mixture having the following culture medium composition, water was added to make the mixture 1 liter in total amount (pH: 7.0) to prepare the culture medium.

| | | |
|---|---|---|
| Oleic acid (carbon source) | 25 g | |
| Yeast extract | 20 g | |
| $KH_2PO_4$ | 1.5 g | |
| $K_2HPO_4$ | 1.5 g | |
| $MgSO_4.7H_2O$ | 0.1 g | |

After the culturing was completed, the bacterial body was collected by centrifugation. A portion of the wet bacterial body thus collected was dispensed for its use in analysis and evaluation, and then washed once with cold methanol, followed by freeze-drying to obtain freeze-dried pellets.

In regard to the remaining wet bacterial body, it was suspended in an aqueous solution of about 1.7% of sodium hypochlorite, which was then shaked at about 4° C. for 2 hours to extract a PHA. The PHA was collected by centrifugation, followed by drying, so that the PHA was obtained in an amount of 1.25 g per 1 L of the culture medium solution. This PHA was designated as PHA1, and was used as a binder resin.

The PHA was also analyzed in the following way. The freeze-dried pellets obtained in the manner described above were subjected to extraction with chloroform at 50° C. for 2 hours. After the bacterial body was removed, methanol was added to the chloroform extract in a 10-fold quantity to collect a PHA by precipitation. The PHA thus obtained was subjected to methanolysis under acidic conditions of sulfuric acid at 100° C. for 140 minutes to convert monomers into methyl esters, and was then put to a gas chromatography mass spectrometer (GC-MS; apparatus: Shimadzu QP-5050; column: DB-WAX, J & W Co., 0.32 mm×30 m; EI method) to make identification of the methyl-esterified products of PHA monomer units. As the result, a two-component type copolymer of 3HB(C4):3HHx(C6)=85:15 was obtained.

The molecular weight of this PHA was also evaluated by gel permeation chromatography (GPC: Toso HLC-8020; column: Polymer Laboratory PLgel MIXED-C, 5 μm; solvent: chloroform; in terms of polystyrene). As the result, its molecular weight was found to be Mn=125,000 and Mw=243,000.

Example 2

An experiment was made in the same manner as in Example 1 except that the oleic acid as a carbon source was used in a concentration of 1 g/L. As the result, a two-component type copolymer of 3HB(C4):3HHx(C6)=70:30 was obtained. This PHA was designated as PHA2, and was used as a binder resin. The molecular weight of this PHA was also found to be Mn=115,000 and Mw=251,000.

Example 3

An experiment was made in the same manner as in Example 1 except that, as the carbon source, lauric acid was used in a concentration of 16 g/L and tridecanoic acid in a concentration of 4 g/L. As the result, a three-component type copolymer of 3HB(C4):3HV(C5):3HHx(C6)=75:10:15 was obtained. This PHA was designated as PHA3, and was used as a binder resin. The molecular weight of this PHA was also found to be Mn=119,000 and Mw=251,000.

Example 4

An experiment was made in the same manner as in Example 1 except that, as the carbon source, lauric acid was used in a concentration of 12 g/L and tridecanoic acid in a concentration of 8 g/L. As the result, a three-component type copolymer of 3HB(C4):3HV(C5):3HHx(C6)=60:30:10 was obtained. This PHA was designated as PHA4, and was used as a binder resin. The molecular weight of this PHA was also found to be Mn=124,000 and Mw=255,000.

Example 5

An experiment was made in the same manner as in Example 1 except that, as the carbon source, lauric acid was used in a concentration of 4 g/L and tridecanoic acid in a concentration of 16 g/L. As the result, a three-component type copolymer of 3HB(C4):3HV(C5):3HHx(C6)=30:65:5 was obtained. This PHA was designated as PHA5, and was used as a binder resin. The molecular weight of this PHA was also found to be Mn=132,000 and Mw=281,000.

Example 6

150 g of polylactic acid (trade name: LACTY; available from Shimadzu Corporation; melt viscosity at 195° C.: 200,000 poises; weight-average molecular weight: 200,000) and 50 g of the PHA of Example 1 (PHA1) were mixed. The mixture formed was put into an injection molding machine, and was melt-kneaded at temperature of 195 to 230° C. and molded. The polymer blend thus obtained was designated as PHA6, and was used as a binder resin.

Example 7

120 g of polylactic acid (trade name: LACTY; available from Shimadzu Corporation; melt viscosity at 195° C.: 200,000 poises; weight-average molecular weight: 200,000) and 80 g of the PHA of Example 1 (PHA1) were mixed. The mixture formed was put into an injection molding machine, and was melt-kneaded at temperature of 195 to 230° C. and molded. The polymer blend thus obtained was designated as PHA7, and was used as a binder resin.

Example 8

150 g of polylactic acid (trade name: LACTY; available from Shimadzu Corporation; melt viscosity at 195° C.: 200,000 poises; weight-average molecular weight: 200,000) and 50 g of the PHA of Example 4 (PHA4) were mixed. The mixture formed was put into an injection molding machine, and was melt-kneaded at temperature of 195 to 230° C. and molded. The polymer blend thus obtained was designated as PHA8, and was used as a binder resin.

Example 9

|  | (by weight) |
|---|---|
| PHA1 (Example 1) | 100 parts |
| Magenta pigment (C.I. Pigment Red 114) | 5 parts |
| Charge control agent (NXVP434, available from Hoechst Japan Ltd.) | 2 parts |

Materials formulated as shown above were melt-kneaded by means of a twin-screw extruder (L/D: 30). The kneaded product thus obtained was cooled, thereafter the cooled product was crushed using a hammer mill, and then the crushed product was finely pulverized by means of a jet mill, followed by classification to obtain magenta colored particles (1) by pulverization. Particle size of the magenta colored particles (1) thus obtained was measured by the method described previously in the present specification, to find that it had a weight-average particle diameter of 7.3 μm and a fine-powder content of 6.2% by number.

In 100 parts by weight of the magenta colored particles (1), 1.5 parts by weight of hydrophobic fine silica powder having been treated with hexamethyldisilazane (BET specific surface area: 250 m$^2$/g) was dry-mixed as a fluidity improver by means of a Henschel mixer to obtain a magenta toner 1 of this Example. Further, 7 parts by weight of the magenta toner 1 thus obtained and 93 parts by weight of a resin-coated magnetic ferrite carrier (average particle diameter: 45 μm) were blended to prepare a two-component magenta developer 1 for magnetic-brush development.

Examples 10 to 16

Magenta toners 2 to 8 of Examples 10 to 16, respectively, were obtained in the same manner as in Example 9 except that 100 parts by weight of PHA2 to PHA8, respectively, were used in place of PHA1. Characteristics of these toners were measured in the same manner as in Example 9 to obtain the results shown in Table 1. Also, using these toners, two-component magenta developers 2 to 8, respectively, were prepared in the same manner as in Example 9.

Comparative Example 1

A magenta toner 9 of Comparative Example 1 was obtained in the same manner as in Example 9 except that 100 parts by weight of styrene-butyl acrylate copolymer resin (glass transition temperature: 70° C.) was used in place of PHA1. Characteristics of this toner were measured in the same manner as in Example 9 to obtain the results shown in Table 1. Also, using this toner, a two-component magenta developer 9 of Comparative Example 1 was prepared in the same manner as in Example 9.

Evaluation

On the two-component magenta developers 1 to 8 obtained in Examples 9 to 16 and the two-component magenta developer 9 obtained in Comparative Example 1, the charge quantity of each toner after agitation for 10 seconds and 300 seconds was measured in each environment of normal temperature and normal humidity (25° C., 60% RH) and high temperature and high humidity (30° C., 80% RH) by the method described previously for measuring charge quantity. Then, from the measured values of two-component blow-off charge quantity, the fractions to two decimal places were round off, and the charging performance was evaluated according to the criteria shown below. The results are shown together in Table 1.

TABLE 1

Charging Performance of Magenta Toners 1 to 9

| | | | Particle Diameter Distribution | | Charging Performance | | | |
|---|---|---|---|---|---|---|---|---|
| | | | | | Normal Temperature and Humidity (Q/M) | | High Temperature and Humidity (Q/M) | |
| Example | PHA No. | Toner No.: Red | Weight- Average Particle Diameter (μm) | Amount of Fine Powder (% by number) | 10- Second Agitation | 300- Second Agitation | 10- Second Agitation | 300- Second Agitation |
| 9 | 1 | 1 | 7.3 | 6.2 | AA | AA | AA | AA |
| 10 | 2 | 2 | 7.1 | 5.5 | AA | AA | AA | AA |

TABLE 1-continued

Charging Performance of Magenta Toners 1 to 9

| Example | PHA No. | Toner No.: Red | Particle Diameter Distribution | | Charging Performance | | | |
|---|---|---|---|---|---|---|---|---|
| | | | | | Normal Temperature and Humidity (Q/M) | | High Temperature and Humidity (Q/M) | |
| | | | Weight-Average Particle Diameter (μm) | Amount of Fine Powder (% by number) | 10-Second Agitation | 300-Second Agitation | 10-Second Agitation | 300-Second Agitation |
| 11 | 3 | 3 | 7.9 | 5.6 | A | AA | A | AA |
| 12 | 4 | 4 | 9.1 | 4.2 | A | AA | A | AA |
| 13 | 5 | 5 | 12.2 | 2.7 | A | A | A | A |
| 14 | 6 | 6 | 6.9 | 5.3 | AA | AA | AA | AA |
| 15 | 7 | 7 | 7.0 | 5.2 | AA | AA | AA | AA |
| 16 | 8 | 8 | 7.3 | 5.1 | AA | AA | AA | AA |
| Comparative Example 1 | — | 9 | 7.0 | 4.9 | AA | AA | AA | AA |

(Charging performance)
AA: Very good (less than −20 μC/g).
A: Good (−20 μC/g to less than −10.0 μC/g).
B: Permissible for practical use (−9.9 μC/g to less than −5.0 μC/g).
C: Inferior (−4.9 μC/g or more).

Examples 17 to 24

Black toners 1 to 8 of Examples 17 to 24, respectively, were obtained in the same manner as in Example 9 except that 100 parts by weight of PHA1 to PHA8, respectively, were used and carbon black (DBP oil absorption: 110 mL/100 g) was used in place of the magenta pigment. Characteristics of these toners were measured in the same manner as in Example 9 to obtain the results shown in Table 2. Also, using these toners, two-component black developers 1 to 8, respectively, were prepared in the same manner as in Example 9.

Comparative Example 2

A black toner 9 of Comparative Example 2 was obtained in the same manner as in Example 9 except that 100 parts by weight of styrene-butyl acrylate copolymer resin (glass transition temperature: 70° C.) was used in place of PHA1 and carbon black (DBP oil absorption: 110 mL/100 g) was used in place of the magenta pigment. Characteristics of these toners were measured in the same manner as in Example 9 to obtain the results shown in Table 2. Also, using this toner, a two-component black developer 9 was prepared in the same manner as in Example 9.

Evaluation

On the two-component black developers 1 to 8 obtained in Examples 17 to 24 and the two-component black developer 9 obtained in Comparative Example 2, the charge quantity of each toner after agitation for 10 seconds and 300 seconds was measured in each environment of normal temperature and normal humidity (25° C., 60% RH) and high temperature and high humidity (30° C., 80% RH) by the method described previously for measuring charge quantity. Then, from the measured values of two-component blow-off charge quantity, the fractions to two decimal places were round off, and the charging performance was evaluated according to the criteria shown below. The results are shown together in Table 2.

TABLE 2

Charging Performance of Black Toners 1 to 9

| Example | PHA No. | Toner No.: Red | Particle Diameter Distribution | | Charging Performance | | | |
|---|---|---|---|---|---|---|---|---|
| | | | | | Normal Temperature and Humidity (Q/M) | | High Temperature and Humidity (Q/M) | |
| | | | Weight-Average Particle Diameter (μm) | Amount of Fine Powder (% by number) | 10-Second Agitation | 300-Second Agitation | 10-Second Agitation | 300-Second Agitation |
| 17 | 1 | 1 | 7.1 | 5.7 | AA | AA | AA | AA |
| 18 | 2 | 2 | 7.0 | 5.4 | AA | AA | AA | AA |
| 19 | 3 | 3 | 7.8 | 5.3 | A | AA | A | AA |

TABLE 2-continued

Charging Performance of Black Toners 1 to 9

| | | | Particle Diameter Distribution | | Charging Performance | | | |
|---|---|---|---|---|---|---|---|---|
| | | | | | Normal Temperature and Humidity (Q/M) | | High Temperature and Humidity (Q/M) | |
| Example | PHA No. | Toner No.: Red | Weight-Average Particle Diameter (μm) | Amount of Fine Powder (% by number) | 10-Second Agitation | 300-Second Agitation | 10-Second Agitation | 300-Second Agitation |
| 20 | 4 | 4 | 9.5 | 4.0 | A | AA | A | AA |
| 21 | 5 | 5 | 11.1 | 2.5 | A | A | A | A |
| 22 | 6 | 6 | 7.2 | 5.0 | AA | AA | AA | AA |
| 23 | 7 | 7 | 7.2 | 5.1 | AA | AA | AA | AA |
| 24 | 8 | 8 | 7.4 | 5.3 | AA | AA | AA | AA |
| Comparative Example 2 | — | 9 | 7.1 | 5.1 | AA | AA | AA | AA |

(Charging performance)
AA: Very good (less than −20 μC/g).
A: Good (−19.9 to less than −10.0 μC/g).
B: Permissible for practical use (−9.9 μC/g to −5.0 μC/g).
C: Inferior (−4.9 μC/g or more).

Example 25

Deinkability Test (The removal of toner from paper surface is herein compared to "deinking".)

Using each of the black toners 1 to 9 obtained in Examples 17 to 24 and Comparative Example 2, a testing image of 6% in black-and-white ratio (image area percentage) was formed on the surface of paper of 75 g/m² in basis weight to make testing paper. Using this testing paper, hand-made sheets for evaluation were prepared under the following conditions.

Defiberization: An aqueous dispersion composed of the following is stirred in a beaker at 50° C. for 20 minutes to defiberize the testing paper.

| Testing paper | 5.0% |
|---|---|
| NaOH | 0.7% |
| Sodium silicate | 3.0% |
| H₂O₂ | 1.0% |

Deinking agent (LIPTOL S 2800, trade name; available from

| Lion Corporation | 0.2% |
|---|---|

Dilution, dehydration and kneader treatment: The above aqueous dispersion is diluted with water to a 5% dispersion, which is then subjected to centrifugal dehydration. Pulp, sodium silicate and so forth are further so added that the pulp is in a content of 20%, the sodium silicate 3.0% and NaOH 0.5%, to carry out defiberization by means of a kneader.

Aging: The kneader-defiberized product is aged at 50° C. for 2 hours.

Flotation: Water is added to the aged product to prepare a dispersion with a pulp concentration of 1%. Into the dispersion, minute air bubbles are released for 7 minutes to make the air bubbles adsorb the toner in the dispersion to allow the latter to come up to the surface, where the toner and the water are separated.

Washing: 2.4 g of the deinked pulp is washed twice with 1 liter of water for each.

Preparation of testing hand-made sheets: Hand-made sheets (basis weight: 100 g/m²) are prepared by means of a TAPPI standard sheet machine.

Evaluation of deinkability: The number of toner particles present in 9 cm² of each hand-made sheet is both visually and microscopically observed to make evaluation individually for two groups of size, 100 μm or more (the size in which the particles are visible to the naked eye) and 60 μm to less than 100 μm.

The results of the above test are shown in Table 3. In Table 3, numerical values indicate the number of remaining toner particles.

TABLE 3

Deinkability Test Results

| | Number of particles | | |
|---|---|---|---|
| | 60 to <100 μm | 100 μm or more | Total |
| Example: | | | |
| 17 | 5 | 9 | 14 |
| 18 | 7 | 9 | 16 |
| 19 | 9 | 3 | 12 |
| 20 | 8 | 7 | 15 |
| 21 | 4 | 8 | 12 |
| 22 | 14 | 10 | 24 |
| 23 | 12 | 13 | 25 |
| 24 | 11 | 9 | 20 |
| Comparative Example: | | | |
| 2 | 43 | 38 | 81 |

Example 26
Biodegradability Test

The red (magenta) toners 1 to 8, the black toners 1 to 8, the comparative red toner 9 and the comparative black toner 9 were melt-shaped into films of about 50 μm in thickness, which were then left in soil for 6 months. As the result, the films of the red toners 1 to 5 and black toners 1 to 5 had completely disappeared in shape, and the films of the red toners 6 to 8 and black toners 6 to 8 had disappeared in its greater part. On the other hand, the comparative red toner 9 and the comparative black toner 9 stood remained in shape as they were.

Examples 27 to 42 & Comparative Examples 3 and 4

An image-forming apparatus used in image-forming processes in Examples 27 to 42 and Comparative Examples 3 and 4 is described first. FIG. 1 is a schematic sectional illustration of an image-forming apparatus for carrying out image-forming processes in Examples and Comparative Examples of the present invention.

As shown in FIG. 1, a photosensitive drum 1 comprises a substrate 1b and provided thereon a photosensitive layer 1a having an organic photo-semiconductor, and is so constructed as to be rotated in the direction of an arrow. By means of a charging roller 2 which is a charging member facing the photosensitive drum 1 and rotated in contact with the drum, the surface of the photosensitive drum is electrostatically charged to have a surface potential of about –600 V. As shown in FIG. 1, the charging roller 2 is constituted of a mandrel 2b and a conductive elastic layer 2a covered thereon.

Figure 2:
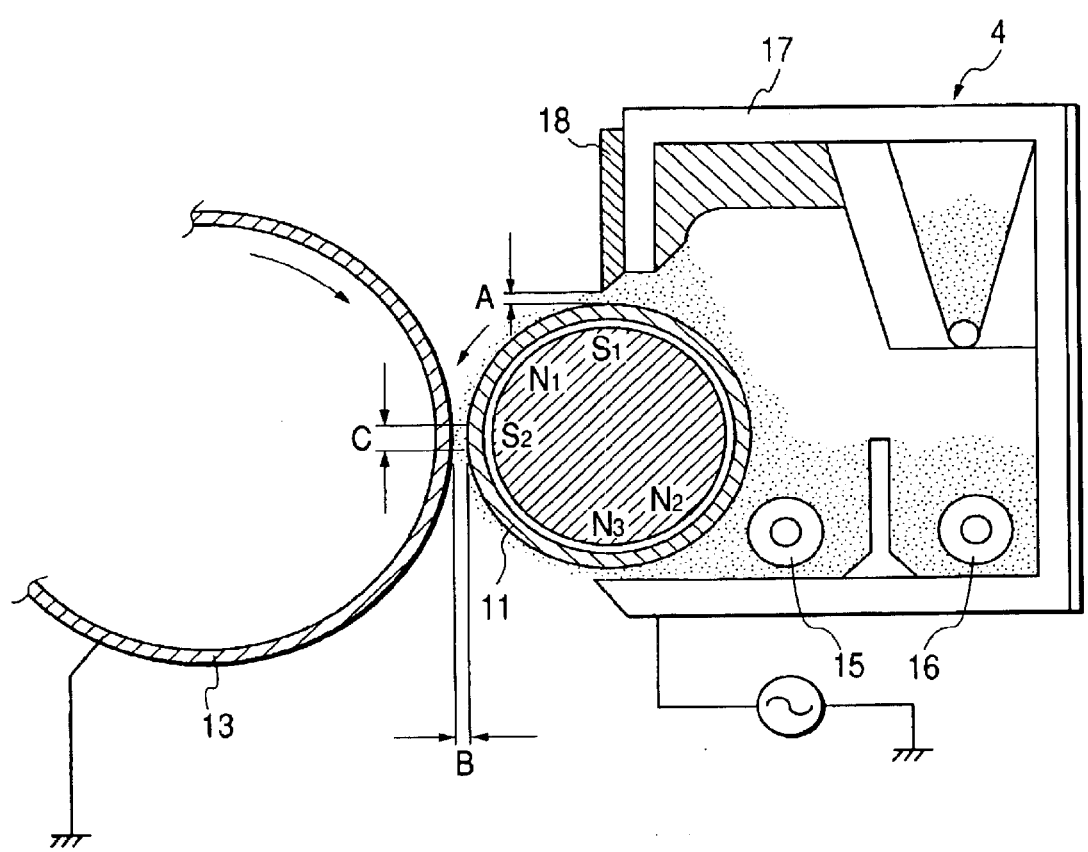
FIG. 2 is a sectional view of the main part of a developing assembly for two-component developer, used in Examples 27 to 42 and Comparative Examples 3 and 4.

Next, the photosensitive drum 1 whose surface is kept charged is exposed to light 3, where an electrostatic latent image having an exposed-area potential of –100 V and a dark-area potential of –600 V is formed on the photosensitive drum by on-off control in accordance with digital image information through a polygon mirror. Subsequently, the electrostatic latent image formed on this photosensitive drum 1 is rendered visible by reversal development by means of a plurality of developing assemblies (for four colors), 4-1, 4-2, 4-3 and 4-4, so that four-color toner images are formed on the photosensitive drum 1. Here, as a magenta or black developer, the two-component developers obtained in Examples 9 to 24 and Comparative Examples 1 and 2 are each used, and toner images are formed using each of the magenta toners or black toners. FIG. 2 is an enlarged sectional view of the main part of each developing assembly 4 for two-component developer, used here. Next, the toner images formed on the photosensitive drum 1 are transferred to an intermediate transfer member 5 rotated in contact with the photosensitive drum 1. As the result, four color, color-superimposed visible images are formed on the intermediate transfer member 5. Transfer residual toner having remained on the photosensitive drum 1 without being transferred is collected in a residual toner container 9 by means of a cleaning member 8.

The intermediate transfer member 5 is, as shown in FIG. 1, constituted of a mandrel 5b as a support and an elastic layer 5a layered thereon. In the present Examples, an intermediate transfer member 5 was used which had a pipe-like mandrel 5b and an elastic layer 5a provided thereon by coating, formed of nitrile-butadiene rubber (NBR) in which carbon black as a conductivity-providing agent had been well dispersed. The elastic layer 5a thus formed had a hardness measured according to JIS K-6301, of 30 degrees and a volume resistivity of $10^9$ Ω·cm. Transfer electric current necessary for the transfer from the photosensitive drum 1 to the intermediate transfer member 5 was about 5 μA, which was obtained by applying a voltage of +500 V to the mandrel 5b from a power source.

The four color, color-superimposed visible images are transferred to a transfer medium such as paper by means of a transfer roller 7, and thereafter fixed by means of a heat-fixing assembly H to come into permanent form. The transfer roller 7 has an elastic layer 7a formed by coating on a mandrel 7b of 10 mm in diameter a foamable material of an ethylene-propylene-diene terpolymer (EPDM) in which carbon black as a conductivity-providing agent has been well dispersed. Here, as the elastic layer 7a, one showing a volume resistivity of 106 Ω·cm and a hardness measured according to JIS K-6301, of 35 degrees was used. A voltage was applied to the transfer roller 7 to flow a transfer current of 15 μA.

Figure 5:
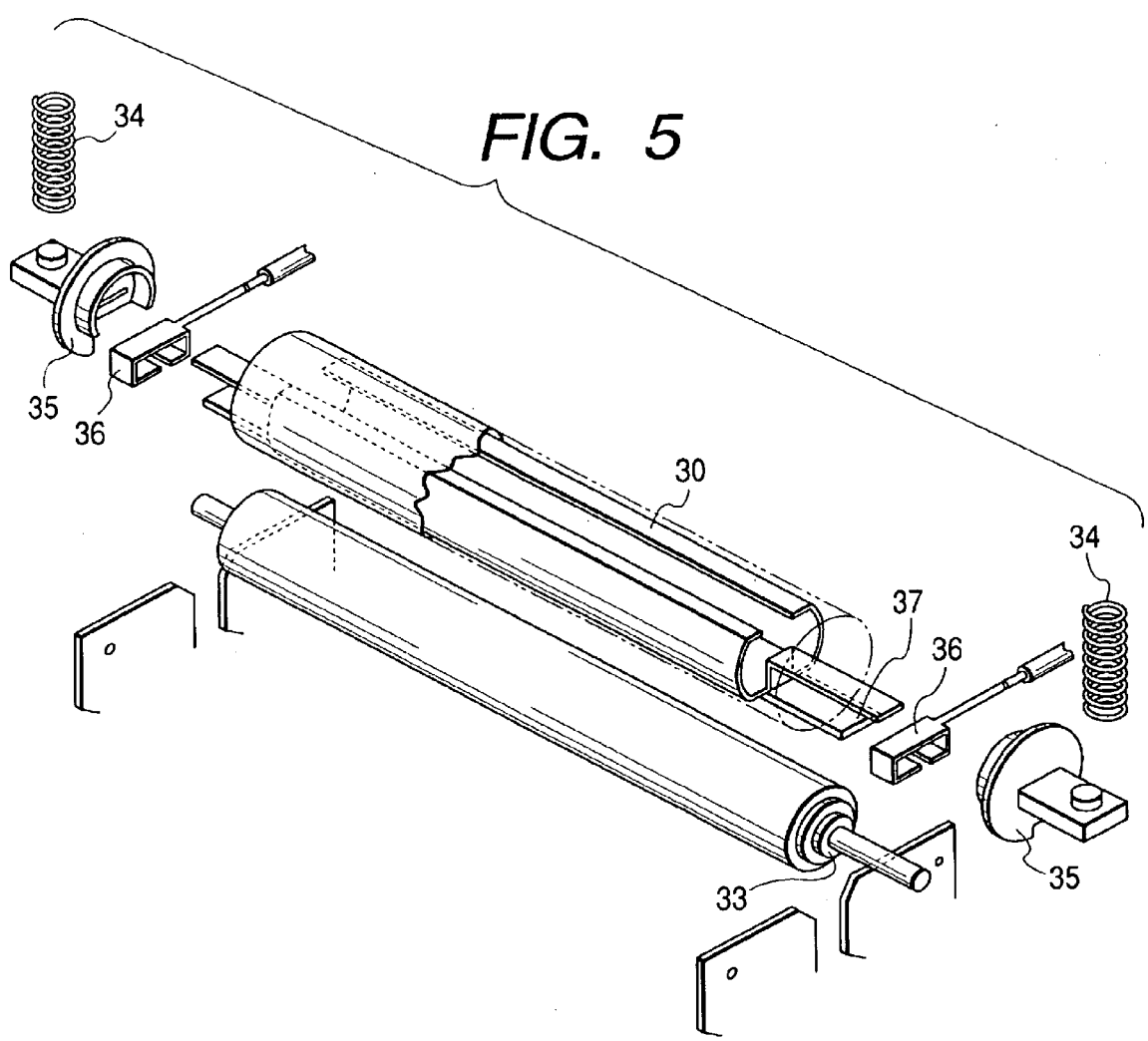
FIG. 5 is an exploded, perspective view of the main part of a fixing assembly used in Examples of the present invention.
Figure 6:
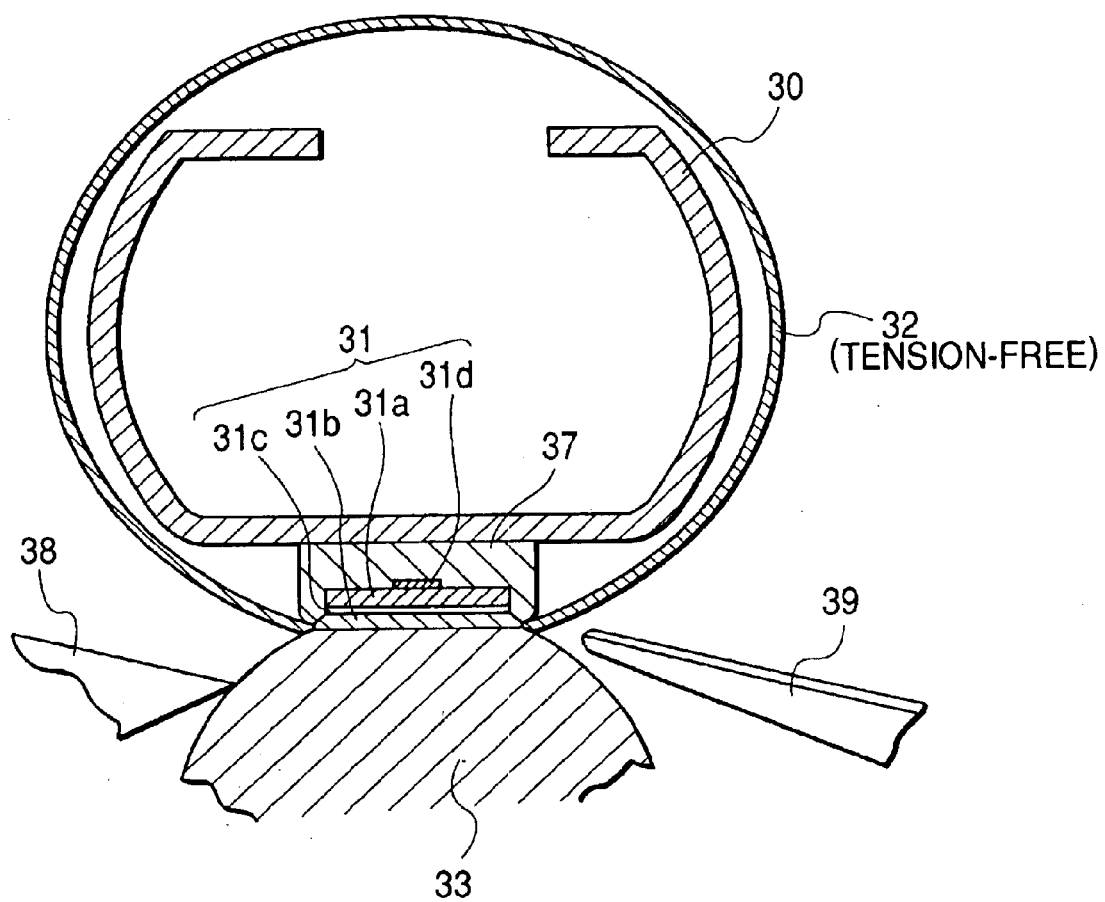
FIG. 6 is an enlarged sectional view of the main part of a fixing assembly used in Examples of the present invention, which shows how a fixing film stands when the fixing assembly is not driven.

In the apparatus shown in FIG. 1, as the heat fixing assembly H, a fixing assembly of a hot-roll type having no mechanism of oil application as shown in FIGS. 5 and 6 is used. Here, as both the upper roller and the lower roller, those having surface layers formed of a fluorine resin were used. The rollers were each in a diameter of 60 mm. The fixing temperature at the time of fixing was set at 160° C., and the nip width at 7 mm. Also, the transfer residual toner on the photosensitive drum 1, having been collected by cleaning, was transported to the developing assemblies by means of a reuse mechanism and was again used.

Evaluation

Under the above conditions, a printing test was made in environments of normal temperature and normal humidity (25° C., 60% RH) and high temperature and high humidity (30° C., 80% RH) at a printing speed of 8 sheets (A4-size)/minute in a monochromatic intermittent mode (i.e., a mode in which the developing assembly was made to pause for 10 seconds every time the images were printed on one sheet so that the deterioration of the toner was accelerated by preliminary operation of the developing assembly when again driven) while successively supplying each of the two-component developers prepared using the toners of Examples 9 to 24 and the two-component developers prepared using the toners of Comparative Examples 1 and 2. Then, evaluation on printed images thus obtained was made in respect of the items shown below. The results of evaluation are shown together in Table 4.

Printed-Image Evaluation

1. Image Density

Evaluated on how image density was maintained on images at the time of finish of printing with respect to images at the initial stage when images were printed on a prescribed number of sheets of usual plain paper (75 g/m²) for copying machines. Here, the image density was measured with Macbeth Reflection Densitometer (manufactured by Macbeth Co.), as relative density with respect to an image printed on a white ground area with a density of 0.00 of an original. The measurements were used in evaluation.

AA: Excellent (the image density at the time of finish is 1.40 or more).

A: Good (the image density at the time of finish is from 1.35 to less than 1.40).

B: Permissible (the image density at the time of finish is from 1.00 to less than 1.35).

C: Inferior (the image density at the time of finish is less than 1.00).

2. Image Fog

Evaluated on how solid white images stood at the time of finish of printing when images were printed on a prescribed number of sheets of usual plain paper (75 g/m²) for copying machines. Stated specifically, it was evaluated in the following way: The worst value of white-background reflection density after printing, measured with a reflection densitometer (REFLECTOMETER MODEL TC-6DS, manufactured by Tokyo Denshoku Co., Ltd.), was regarded as Ds, and an average value of reflection densities of paper before printing, as Dr. From these values, the value of Ds−Dr was found and this was regarded as the amount of fog to make evaluation according to the following criteria.

scratching of the surfaces of the photosensitive drum and intermediate transfer member nor sticking of remaining toner was not seen at all in systems in which the two-component developers other than those of Examples 30, 31, 38 and 39 were used, showing very good matching with the image-forming apparatus.

In the systems in which the two-component developers of Examples 30, 31, 38 and 39 were used, the scratching of the surfaces of the photosensitive drum and intermediate transfer member or the sticking of remaining toner was seen to have slightly occurred, but there was no problem in practical use.

TABLE 4

Printed-Image Evaluation Results

| Example | Two-component Developer | Normal Temperature and Humidity | | | High Temperature and Humidity | | |
|---|---|---|---|---|---|---|---|
| | | Image Density | Image Fog | Transfer Performance | Image Density | Image Fog | Transfer Performance |
| 27 | Red 1 | AA | AA | AA | AA | AA | AA |
| 28 | Red 2 | AA | AA | AA | AA | AA | AA |
| 29 | Red 3 | AA | A | AA | AA | A | A |
| 30 | Red 4 | A | A | A | A | B | B |
| 31 | Red 5 | A | B | B | A | B | B |
| 32 | Red 6 | AA | AA | AA | AA | AA | AA |
| 33 | Red 7 | AA | AA | AA | AA | AA | AA |
| 34 | Red 8 | AA | AA | AA | AA | AA | AA |
| 35 | Black 1 | AA | AA | AA | AA | AA | AA |
| 36 | Black 2 | AA | AA | AA | AA | AA | AA |
| 37 | Black 3 | AA | A | AA | AA | A | A |
| 38 | Black 4 | A | A | A | A | B | B |
| 39 | Black 5 | B | B | B | B | B | B |
| 40 | Black 6 | AA | AA | AA | AA | AA | AA |
| 41 | Black 7 | AA | AA | AA | AA | AA | AA |
| 42 | Black 8 | AA | AA | AA | AA | AA | AA |
| Comparative Example 3 | Red 9 | AA | AA | AA | AA | AA | AA |
| 4 | Black 9 | AA | AA | AA | AA | AA | AA |

AA: Very good (the amount of fog is from 0% to less than 1.5%).

A: Good (the amount of fog is from 1.5% to less than 3.0%).

B: Permissible for practical use (the amount of fog is from 3.0% to less than 5.0%).

C: Inferior (the amount of fog is 5.0% or more).

3. Transfer Performance

Solid black images were printed on a prescribed number of sheets of usual plain paper (75 g/m²) for copying machines, and the level of image blank areas in images at the time of finish of printing was observed to make evaluation according to the following criteria.

AA: Very good (the image blank areas little occur).

A: Good (they occur only slightly).

B: Permissible for practical use.

C: Inferior.

Evaluation was also visually made on whether or not, when images were reproduced on 5,000 sheets in Examples 27 to 42 and Comparative Examples 3 and 4, any scratching of the surfaces of the photosensitive drum and intermediate transfer member or any sticking of remaining toner occurred and how these affected the printed images (i.e., matching with image-forming apparatus). As the result, neither Examples 43 to 48 and Comparative Examples 5 and 6

Figure 3:
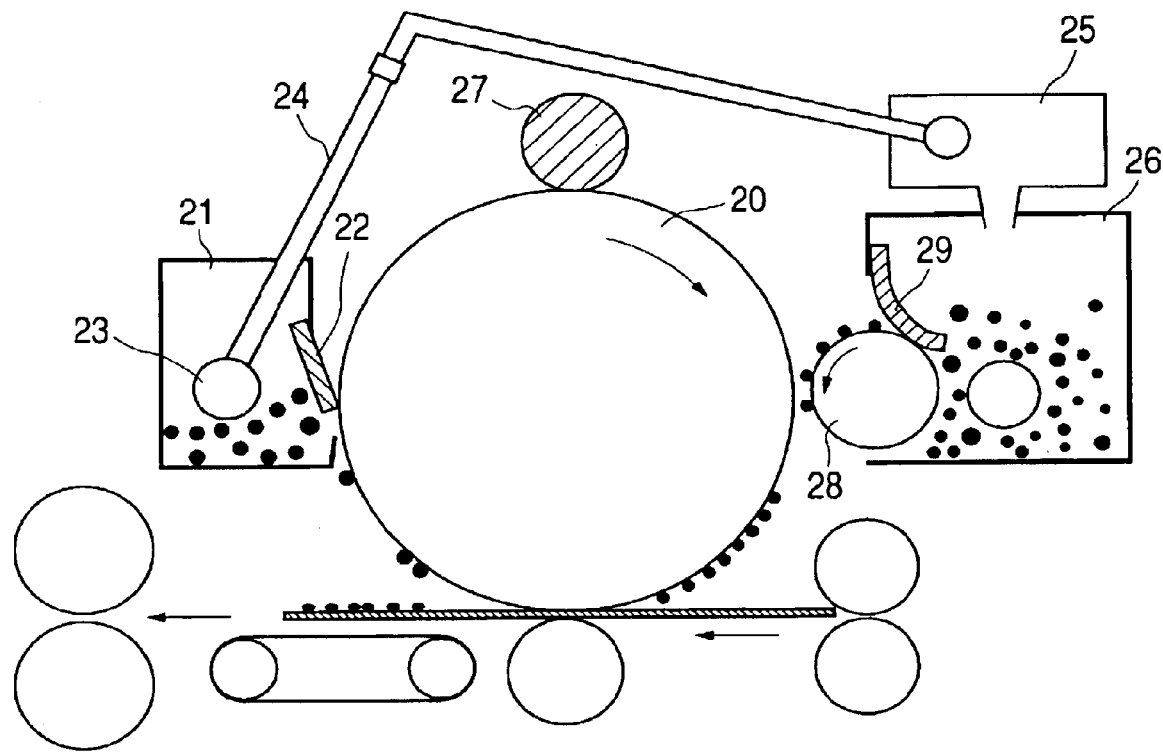
FIG. 3 is a schematic illustration of an image-forming apparatus having a toner reuse mechanism, used in Examples 43 to 48 and Comparative Examples 5 and 6.

In carrying out image-forming processes in Examples 43 to 48 and Comparative Examples 5 and 6, the toners obtained in Examples 17 to 19 and 22 to 24 and Comparative Examples 1 and 2 were used as developers, respectively. As a means for forming images, an image-forming apparatus was used in which as shown in FIG. 3 a reuse mechanism was attached to a commercially available laser beam printer LBP-EX (manufactured by CANON INC.) to remodel the printer, which was again set up and used. More specifically, the image-forming apparatus shown in FIG. 3 is fitted with a system in which the untransferred toner having remained on the surface of a photosensitive drum 20 after transfer is scraped off with an elastic blade 22 of a cleaner 21, coming into touch with the photosensitive drum 20, and is sent into the cleaner 21, where the toner thus collected is further transported through a cleaner screw 23 by means of a feed pipe 24 provided with a transport screw, and, through a hopper 25, returned to a developing assembly 26, and the toner thus collected is again used for development.

In the the image-forming apparatus shown in FIG. 3, the surface of the photosensitive drum 20 is electrostatically charged by means of a primary charging roller 27. In the primary charging roller 27, used is a rubber roller (diameter:

12 mm; contact pressure: 50 g/cm) in which conductive carbon has been dispersed, and covered with a nylon resin. On the electrostatic latent image bearing member (photosensitive drum 20), an electrostatic latent image with a dark-area potential $V_D$ of −700 V and a light-area potential $V_L$ of −200 V were formed by laser exposure (600 dpi, not shown). As a toner carrying member, a developing sleeve 28 whose surface was coated with a resin having carbon black dispersed therein and had a surface roughness Ra of 1.1 was used.

Figure 4:
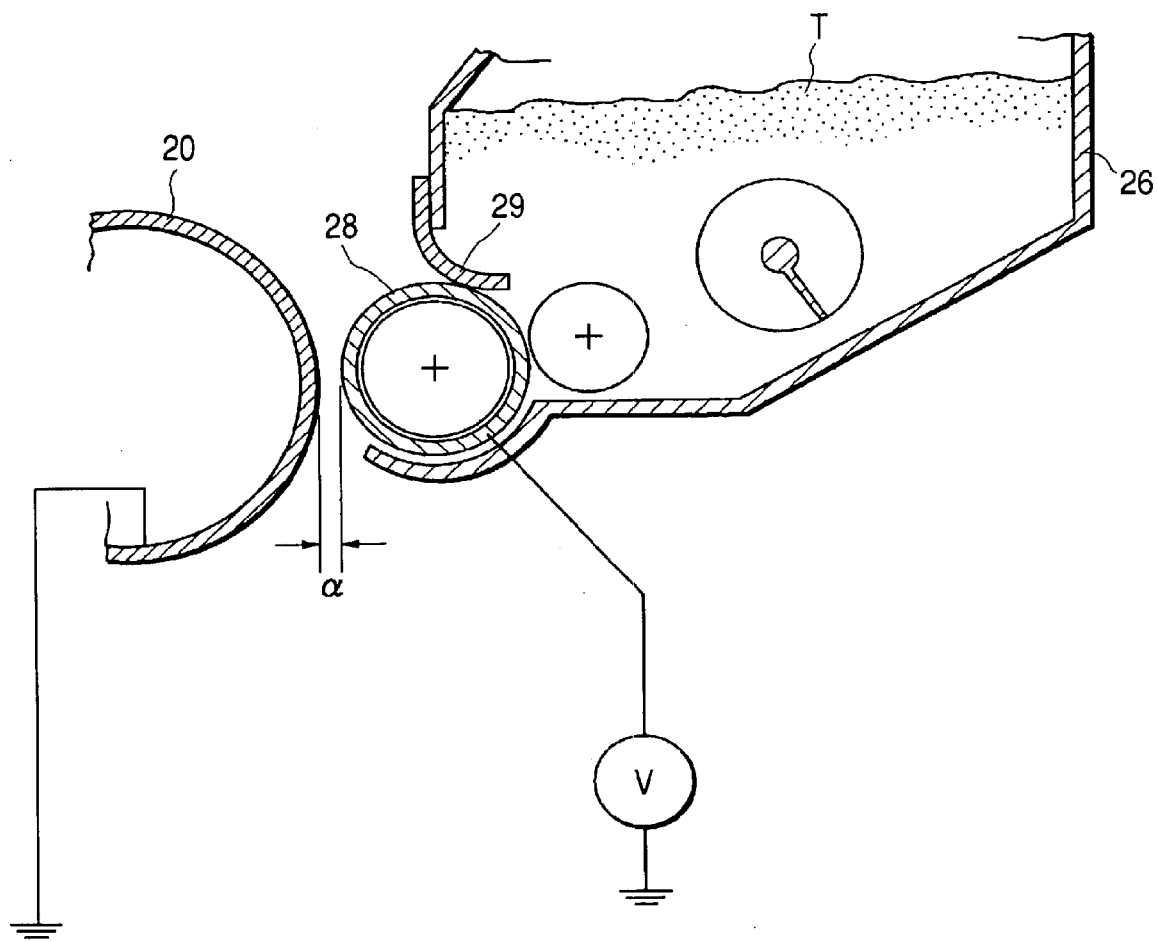
FIG. 4 is a sectional view of the main part of a developing assembly for one-component developer, used in Examples 43 to 48 and Comparative Examples 5 and 6.

In FIG. 4, shown is a sectional view of the main part of a developing assembly for one-component developer, used in Examples 43 to 48 and Comparative Examples 5 and 6. As conditions for developing electrostatic latent images, the surface movement speed of the developing sleeve 28 was so set as to be 1.1 times the movement speed of the photosensitive drum 20 surface, and also the gap α (S–D distance) between the photosensitive drum 20 and the developing sleeve 28 was set to be 270 μm. As a toner layer thickness regulation member, a blade 29 made of urethane rubber was used in contact with the developing sleeve. Also, the temperature of the heat-fixing assembly for fixing toner images was set at 160° C. As the fixing assembly, a fixing assembly (a fixing film type) shown in FIGS. 5 and 6 was used.

Under the above conditions, a printing test was made on up to 30,000 sheets in an environment of normal temperature and normal humidity (25° C., 60% RH) at a printing speed of 8 sheets (A4-size)/minute in a continuous mode (i.e., a mode in which the developing assembly was not made to pause so that the deterioration of the toner was accelerated) while successively supplying the toner. On the printed images thus formed, their image density was measured and how the image density changed during running was examined to make evaluation according to the criteria shown below. Also, images on the 10,000th sheet were observed and evaluation on image fog was made according to the criteria shown below. At the same time, how the units constituting the image-forming apparatus stood after the running test was also observed to make evaluation also on the matching of the respective toners with the units.

The results of the foregoing are shown together in Table 5.

Change in image density during running:

Evaluated on how image density was maintained on images at the time of finish of printing with respect to images at the initial stage when images were printed on a prescribed number of sheets of usual plain paper (75 g/m²) for copying machines. Here, the image density was measured with Macbeth Reflection Densitometer (manufactured by Macbeth Co.), as relative density with respect to an image printed on a white ground area with a density of 0.00 of an original. The measurements were used in evaluation.

AA: Excellent (the image density at the time of finish is 1.40 or more).

A: Good (the image density at the time of finish is from 1.35 to less than 1.40).

B: Passable (the image density at the time of finish is from 1.00 to less than 1.35).

C: Failure (the image density at the time of finish is less than 1.00).

Image Fog

Evaluated on how solid white images stood at the time of finish of printing when images were printed on a prescribed number of sheets of usual plain paper (75 g/m²) for copying machines. Stated specifically, it was evaluated in the following way: The worst value of white-background reflection density after printing, measured with a reflection densitometer (REFLECTOMETER MODEL TC-6DS, manufactured by Tokyo Denshoku Co., Ltd.), was regarded as Ds, and an average value of reflection densities of paper before printing, as Dr. From these values, the value of Ds−Dr was found and this was regarded as the amount of fog to make evaluation according to the following criteria.

AA: Very good (the amount of fog is from 0% to less than 1.5%).

A: Good (the amount of fog is from 1.5% to less than 3.0%).

B: Permissible for practical use (the amount of fog is from 3.0% to less than 5.0%).

C: Inferior (the amount of fog is 5.0% or more).

Evaluation on Matching with Image Forming Apparatus

1. Matching with Developing Sleeve

After the printing test was finished, evaluation was visually made by examining any sticking of the toner remaining on the developing-sleeve surface and how it affected the printed images.

AA: Very good (no sticking occurs).

A: Good (sticking little occurs).

B: Permissible for practical use (sticking occurs, but less affects images).

C: Inferior (sticking occurs greatly, and uneven images occur).

2. Matching with Photosensitive Drum

Evaluation was visually made by examining any scratching of the photosensitive-drum surface and any sticking of the toner remaining thereon, and how they affected the printed images.

AA: Very good (none of them occurs).

A: Good (scratches are seen to slightly occur, but do not affect images).

B: Permissible for practical use (sticking and scratches are seen, but less affect images).

C: Inferior (sticking occurs greatly, and faulty images occur as vertical lines).

3. Matching with Fixing Assembly

How the fixing-film surface stood was observed, and the results on its surface properties and any sticking of the toner remaining on its surface were overall averaged to evaluate its durability.

(1) Surface Properties

After the printing test was finished, evaluation was made by visually observing any scratching or abrasion of the fixing-film surface.

AA: Very good (none of them occurs).

A: Good (they little occur).

B: Permissible for practical use.

C: Inferior.

(2) Sticking of Remaining Toner

After the printing test was finished, evaluation was made by visually observing any sticking of the toner remaining on the fixing-film surface.

AA: Very good (no sticking occurs).

A: Good (sticking little occurs).

B: Permissible for practical use.

C: Inferior.

TABLE 5

Printed-Image Evaluation Results and Matching with Image-Forming Apparatus

| | | Evaluation of Printed Image | | | | | Evaluation of Matching with constituent units | | | |
|---|---|---|---|---|---|---|---|---|---|---|
| | | Change in Image Density during running | | | | Image Fog | Developing Sleeve | Photosensitive Drum | Fixing Assembly | |
| | | | | | | | | | Surface Properties | Sticking of Toner |
| Example | Toner | Initial Print | 1000th Print | 10,000th Print | 30,000th Print | 10,000th Print | | | | |
| 43 | Black 1 | AA | AA | AA | AA | AA | AA | AA | AA | AA |
| 44 | Black 2 | AA | AA | AA | AA | AA | AA | AA | AA | AA |
| 45 | Black 3 | AA | AA | AA | A | AA | AA | A | AA | A |
| 46 | Black 6 | AA | AA | AA | AA | AA | AA | AA | AA | AA |
| 47 | Black 7 | AA | AA | AA | AA | AA | AA | AA | AA | AA |
| 48 | Black 8 | AA | AA | AA | AA | AA | AA | AA | AA | AA |
| Comparative Example 5 | Red 9 | AA | AA | AA | AA | AA | AA | AA | AA | AA |
| 6 | Black 9 | AA | AA | AA | AA | AA | AA | AA | AA | AA |

Example 49

Successively supplying the black toner 1 of Example 17, a printing test was made in a continuous mode (i.e., a mode in which the developing assembly was not made to pause so that the consumption of the toner was accelerated), in the same manner as in Example 48 except that the toner reuse mechanism of the FIG. 3 image-forming apparatus was detached and the printing speed was changed to 16 sheets (A4-size)/minute. The printed images obtained and the matching with the image-forming apparatus used were evaluated on the same items as those in Examples 43 to 48 and Comparative Examples 5 and 6. As the result, good results were obtained on all the items.

As having been described above, according to the present invention, the PHA comprised of two kinds of units, the 3-hydroxybutyrate (3HB) unit and the 3-hydroxyhexanoate (3HHx) unit at least, or the PHA comprising the above PHA which further contains at least one unit selected from the 4-hydroxybutyrate (4HB) unit, the 4-hydroxyvalerate (4HV) unit, the 3-hydroxyvalerate (3HV) unit and the 3-hydroxypropionate (3HP) unit is used as a binder resin. This makes it possible to provide a binder resin which has high safety to human bodies and environment, and is biodegradable not to affect the natural environment adversely, and also which enables deinking with ease by a conventionally available deinking process making use of an alkali, to promote the reuse of copying paper having been used, and can satisfy various performances and properties required as toners, e.g., those concerning carrier-spent, fog, charging stability, running performance, storage stability, pulverizability, cost and so forth; a toner for developing electrostatic latent images which comprises such a binder resin; and an image-forming method and an image-forming apparatus which make use of the toner.

What is claimed is:

1. A binder resin composition for toners which comprises a polyhydroxyalkanoate having at least two kinds of units, a 3-hydroxybutyrate (3HB) unit represented by the following formula (1) and a 3-hydroxyhexanoate (3HHx) unit represented by the following formula (2)

(1): 3HB

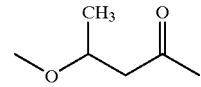

(2): 3HHx

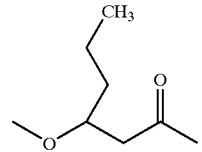

and at least one resin selected from polycaprolactone and polylactic acid.

2. The binder resin composition for toners according to claim 1, wherein said polyhydroxyalkanoate further contains at least one unit selected from a 4-hydroxybutyrate (4HB) unit represented by the following formula (3), a 4-hydroxyvalerate (4HV) unit represented by the following formula (4), a 4-hydroxyvalerate (3HV) unit represented by the following formula (5) and a 3-hydroxypropionate (3HP) unit represented by the following formula (6):

(3): 4HB

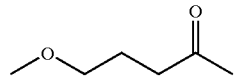

(4): 4HV

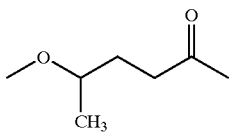

(5): 3HV

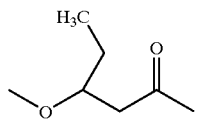

(6): 3HP

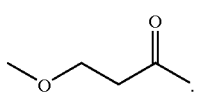

3. The binder resin composition for toners according to claim 1, wherein said 3-hydroxybutyrate (3HB) unit is contained in an amount of 50 mol % to 95 mol %.

4. The binder resin composition for toners according to claim 1, which has a number average molecular weight of 2,000 to 300,000.

5. The binder resin composition for toners according to claim 1, which has a glass transition point of 30° C. to 80° C. and a softening point of 60° C. to 170° C.

6. A toner comprising a binder resin composition, wherein said binder resin composition comprises a polyhydroxyalkanoate having at least two kinds of units, a 3-hydroxybutyrate (3HB) unit represented by the following formula (1) and a 3-hydroxyhexanoate (3HHx) unit represented by the following formula (2):

(1): 3HB

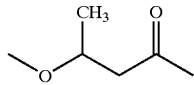

(2): 3HHx

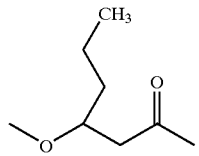

and at least one resin selected from polycaprolactone and polylactic acid.

7. An image-forming method comprising the steps of:
a charging step of applying a voltage to a charging member from its outside to charge an electrostatic-latent-image-bearing member electrostatically;
a latent-image-forming step of forming an electrostatic latent image on the electrostatic-latent-image-bearing member thus charged;
a developing step of developing the electrostatic latent image by the use of a toner for developing electrostatic latent images, to form a toner image on the electrostatic-latent-image-bearing member;
a transfer step of transferring to a recording medium the toner image formed on the electrostatic-latent-image-bearing member; and
a fixing step of fixing by heat the toner image held on the recording medium;
wherein said toner comprises a binder resin composition, and the binder resin composition comprises a polyhydroxyalkanoate having at least two kinds of units, a 3-hydroxybutyrate (3HB) unit represented by the following formula (1) and a 3-hydroxyhexanoate (3HHx) unit represented by the following formula (2):

(1): 3HB

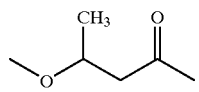

(2): 3HHx

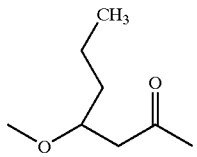

and at least one resin selected from polycaprolactone and polylactic acid.

8. An image forming method comprising the steps of:
a charging step of applying a voltage to a charging member from its outside to charge an electrostatic-latent-image-bearing member electrostatically;
a latent-image-forming step of forming an electrostatic latent image on the electrostatic-latent-image-bearing member thus charged;
a developing step of developing the electrostatic latent image by the use of a toner for developing electrostatic latent images, to form a toner image on the electrostatic-latent-image-bearing member;
a first transfer step of transferring to an intermediate transfer member the toner image formed on the electrostatic-latent-image-bearing member;
a second transfer step of transferring to a recording medium the toner image held on the intermediate transfer member; and
a fixing step of fixing by heat the toner image held on the recording medium;
wherein said toner comprises a binder resin composition, and the binder resin composition comprises a polyhydroxyalkanoate having at least two kinds of units, a 3-hydroxybutyrate (3HB) unit represented by the following formula (1) and a 3-hydroxyhexanoate (3HHx) unit represented by the following formula (2):

(1): 3HB

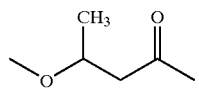

(2): 3HHx

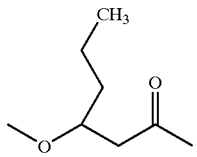

and at least one resin selected from polycaprolactone and polylactic acid.

9. An image-forming apparatus comprising:

charging means for applying a voltage to a charging member from its outside to charge an electrostatic-latent-image-bearing member electrostatically;

latent-image-forming means for forming an electrostatic latent image on the electrostatic-latent-image-bearing member thus charged;

developing means for developing the electrostatic latent image by the use of a toner for developing electrostatic latent images, to form a toner image on the electrostatic-latent-image-bearing member;

transfer means for transferring to a recording medium the toner image formed on the electrostatic-latent-image-bearing member; and fixing means for fixing by heat the toner image held on the recording medium;

wherein said toner comprises a binder resin composition, and the binder resin composition comprises a polyhydroxyalkanoate having at least two kinds of units, a 3-hydroxybutyrate (3HB) unit represented by the following formula (1) and a 3-hydroxyhexanoate (3HHx) unit represented by the following formula (2):

(1): 3HB

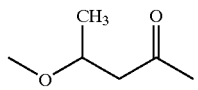

(2): 3HHx

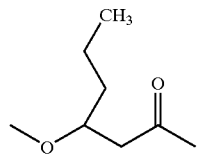

and at least one resin selected from polycaprolactone and polylactic acid.

10. An image-forming further apparatus comprising:

charging means for applying a voltage to a charging member from its outside to charge an electrostatic-latent-image-bearing member electrostatically;

latent-image-forming means for forming an electrostatic latent image on the electrostatic-latent-image-bearing member thus charged;

developing means for developing the electrostatic latent image by the use of a toner for developing electrostatic latent images, to form a toner image on the electrostatic-latent-image-bearing member;

first transfer means for transferring to an intermediate transfer member the toner image formed on the electrostatic-latent-image-bearing member;

second transfer means for transferring to a recording medium the toner image held on the intermediate transfer member; and fixing means for fixing by heat the toner image held on the recording medium;

wherein said toner comprises a binder resin composition, and the binder resin composition comprises a polyhydroxyalkanoate having at least two kinds of units, a 3-hydroxybutyrate (3HB) unit represented by the following formula (1) and a 3-hydroxyhexanoate (3HHx) unit represented by the following formula (2):

(1): 3HB

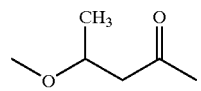

(2): 3HHx

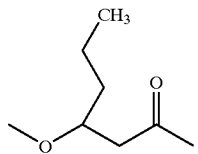

and at least one resin selected from polycaprolactone and polylactic acid.

* * * * *

UNITED STATES PATENT AND TRADEMARK OFFICE
CERTIFICATE OF CORRECTION

PATENT NO. : 6,828,074 B2
DATED : December 7, 2004
INVENTOR(S) : Tetsuya Yano et al.

It is certified that error appears in the above-identified patent and that said Letters Patent is hereby corrected as shown below:

Column 2,
Line 38, "one of" should read -- one of the --.

Column 4,
Line 53, "and and" should read -- and --.

Column 9,
Line 45, "make" should read -- makes --.

Column 12,
Line 14, "butyleneglycoldiacrylate," should read -- butylene glycol diacrylate, --.

Column 15,
Line 12, "pulverizes" should read -- pulverized --.

Column 16,
Line 65, "material" should read -- materials --.

Column 24,
Line 63, (Table 2), "Red" should read -- Black --.

Column 25,
Line 14, (Table 2-continued), "Red" should read -- Black --.

UNITED STATES PATENT AND TRADEMARK OFFICE
CERTIFICATE OF CORRECTION

PATENT NO. : 6,828,074 B2
DATED : December 7, 2004
INVENTOR(S) : Tetsuya Yano et al.

It is certified that error appears in the above-identified patent and that said Letters Patent is hereby corrected as shown below:

Column 28,
Line 1, "$10^9$ Ω•cm." should read -- $10^9 Ω·cm$. --.
Line 15, "106 Ω•cm" should read -- $10^6 Ω·cm$ --.

Signed and Sealed this

Fourteenth Day of June, 2005

JON W. DUDAS
*Director of the United States Patent and Trademark Office*